(12) United States Patent
Winn et al.

(10) Patent No.: US 7,923,433 B2
(45) Date of Patent: Apr. 12, 2011

(54) ACTIVITY-BASED PROBES AND METHODS OF THEIR PREPARATION AND USE

(75) Inventors: David Winn, San Diego, CA (US); David Alan Campbell, San Diego, CA (US)

(73) Assignee: Activx Biosciences, Inc., La Jolla, CA (US)

( * ) Notice: Subject to any disclaimer, the term of this patent is extended or adjusted under 35 U.S.C. 154(b) by 928 days.

(21) Appl. No.: 10/530,646

(22) PCT Filed: Oct. 8, 2003

(86) PCT No.: PCT/US03/32152
§ 371 (c)(1),
(2), (4) Date: Jan. 11, 2006

(87) PCT Pub. No.: WO2004/033397
PCT Pub. Date: Apr. 22, 2004

(65) Prior Publication Data
US 2007/0141624 A1    Jun. 21, 2007

Related U.S. Application Data

(60) Provisional application No. 60/417,664, filed on Oct. 9, 2002.

(51) Int. Cl.
*A61K 38/05* (2006.01)
(52) U.S. Cl. .................................................. 514/21.91
(58) Field of Classification Search .................... None
See application file for complete search history.

(56) References Cited

U.S. PATENT DOCUMENTS

| 6,008,373 | A | 12/1999 | Waggoner et al. | |
| 6,127,134 | A | 10/2000 | Minden et al. | |
| 6,207,397 | B1 * | 3/2001 | Lynch et al. | 435/7.8 |
| 2002/0086333 | A1 * | 7/2002 | Gahunia et al. | 435/7.1 |

FOREIGN PATENT DOCUMENTS

| CA | 2475653 | 9/2003 |
| WO | WO-98/36057 | 8/1998 |
| WO | WO-00/01666 | 1/2000 |
| WO | WO-00/23421 | 4/2000 |
| WO | WO-01/08710 | 2/2001 |
| WO | WO 01/77668 | 10/2001 |
| WO | WO 01/77684 | 10/2001 |
| WO | WO 02/063271 | 8/2002 |
| WO | WO-03/072528 | 9/2003 |
| WO | WO 2003/072528 * | 9/2003 |

OTHER PUBLICATIONS

Papanikos et al., "e-Ketocarbonyl Peptides: A General Approach to Reactive Resin-Bound Intermediates in the Synthesis of Peptide Isoteres for Protease Inhibitor Screening on Solid Support." J. Am. Chem. Soc. 123: 2176-2181, (2001).*

Wilbur et al, "Biotin reagents for antibody pretargeting. 5. Additional studies of biotin conjugate design to provide biotinidase stability," Bioconjugate Chemistry (2001), 12(4), 616-623.*

Krantz A, et al, "Peptidyl (acyloxy)methyl ketones and the quiescent affinity label concept: the departing group as a variable structural element in the design of inactivators of cysteine proteinases,".Biochemistry. May 14, 1991;30(19):4678-4687.*

Aladekomo, J. B. et al, "Excimer' Fluorescence. VII. Spectral Studies of Naphthalene and Its Derivatives." Sciences, vol. 284, No. 1399 (Mar. 23, 1965), pp. 551-565.*

Bergseid, M. et al., "Small Molecule-Based Chemical Affinity System for the Purification of Proteins, Biotechniques." 29(5), 1126-1133, (2000).

Brömme, et al. "Human Cathepsin V Functional Expression, Tissue Distribution, Electrostatic Surface Potential, Enzymatic Characterization, and Chromosomal Localization." *Biochemistry* 38: 2377-2385, (1999).

Cull and McHenry, "Preparation of Extracts from Prokaryotes." (in *Methods in Enzymology*, vol. 182, Guide to Protein Purification, edited by Murray P. Deutscher) pp. 147-238, (1990).

Daniel, S. G. et al., "FastTag™ Nucleic Acid Labeling System: A Versatile Method for Incorporating Haptens, Fluorochromes and Affinity Ligands into DNA, RNA and Oligonucleotides." Biotechniques 24(3), 484-489, (1998).

Gottschling et al., "Cellular Solid-Phase Binding Assay and Mass Spectrometry for Screening of α4β7 Integrin Antagonists." Bioorg. And Medicinal Chem. Lett. 11: 2997-3000, (2001).

Gibson et al., "Nonpeptidic αvβ$_3$ Integrin Antagonist Libraries: On-Bead Screening and Mass Spectrometric Identification without Tagging." Agnew. Chem. Int. Ed. 40: 165-169, (2001).

Kidd et al., "Profiling Serine Hydrolase Activities in Complex Proteomes." *Biochemistry* 40: 4005-15, (2001).

Leon et al., "Evaluation of Resins for on-bead Screening: A Study of Papain and Chymotrypsin Specificity Using Pega-Bound Combinatorial Peptide Libraries." Bioorg. Med. Chem. Lett. 8: 2997-3002, (1998).

Orain and Bradley, "Solid phase synthesis of trypanothione reductase inhibitors—towards single bead screening." Tetrahedron Lett. 42: 515-518, (2001).

Papanikos et al., "α-Ketocarbonyl Peptides: A General Approach to Reactive Resin-Bound Intermediates in the Synthesis of Peptide Isoteres for Protease Inhibitor Screening on Solid Support." J. Am. Chem. Soc. 123: 2176-2181, (2001).

Porco, J.A., "Organic Synthesis Using Chemical Tags: The 'Third Leg' Parallel synthesis." Comb. Chem. High Throughput Screening. 3(2) 93-102 (2000).

Smith and Bradley, "Comparison of Resin and Solution Screening Methodologies in Combinatorial Chemistry and the Identification of a 100 nM Inhibitor of Trypanothione Reductase." J. Comb. Med. 1: 326-332, (1999).

Supplementary European Search Report for EP Application No. 03774762.3.

European Office Action dated Dec. 3, 2009 for EP App. No. 03774762.3-1211.

Office Action dated Jun. 11, 2010 for Canadian Application No. 2,501,831.

* cited by examiner

*Primary Examiner* — Cecilia Tsang
*Assistant Examiner* — Thomas S Heard
(74) *Attorney, Agent, or Firm* — Foley & Lardner LLP; Stephen E. Reiter

(57) ABSTRACT

The present invention provides compositions and methods for assessing profiles of catalytically active enzymes in compositions containing a plurality of proteins. In preferred embodiments, the enzyme is a hydrolase, most preferably a cysteine protease. The methods described herein use activity based probes ("ABPs") that have an affinity moiety for directing the binding of the ABP to one or more catalytically active target enzymes, a reactive group for forming a covalent bond at an active site of the target enzyme(s), and a TAG (e.g., a detectable label, preferably a fluorophore). One or more ABPs may be combined with a protein-containing sample under conditions for binding and reaction of the ABP(s) with target enzyme(s) that are present in the sample. The resulting products may then be used to assess the active enzyme profile of the sample, and can be correlated to the presence, amount, or activity of one or more target enzyme(s) present in the original complex protein mixture.

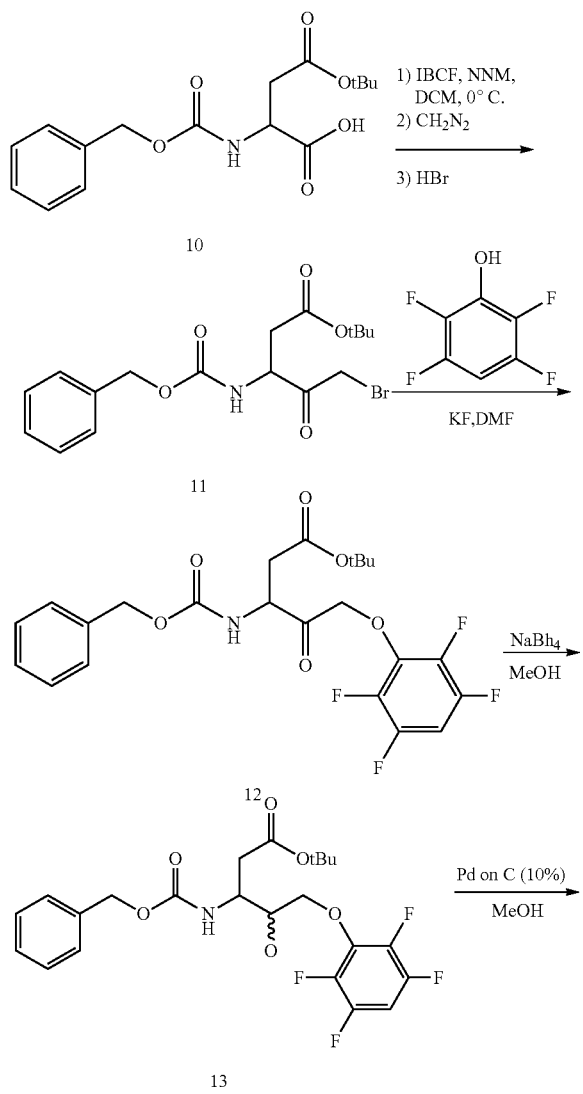

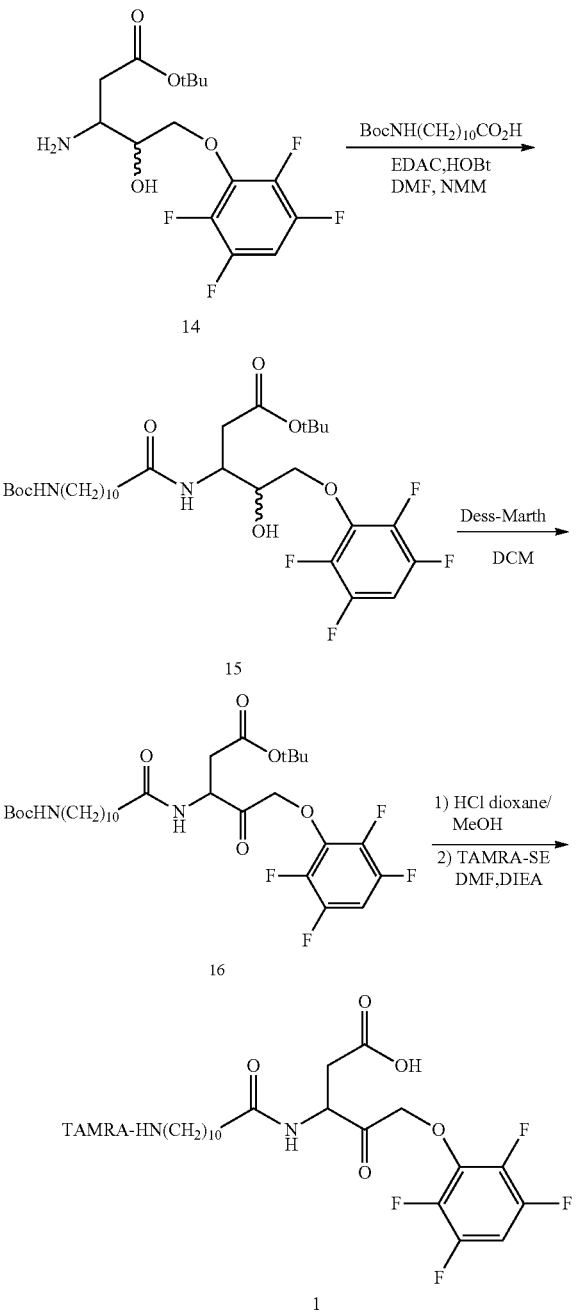

13 Claims, 2 Drawing Sheets

US 7,923,433 B2

ACTIVITY-BASED PROBES AND METHODS OF THEIR PREPARATION AND USE

FIELD OF THE INVENTION

The invention relates generally to affinity labeling of catalytically active enzymes, more preferably hydrolases, and most preferably cysteine proteases.

BACKGROUND

Proteolytic enzymes are involved in a great variety of physiological processes. Proteases are generally classified according to their catalytic mechanisms. At least four mechanistic classes have been recognized, including the serine proteases, the cysteine proteases, the aspartic proteases, and the metalloproteases. The cysteine proteases can be grouped into at least 30 protein families including the plant proteases such as papain, actinidin or bromelain, several mammalian lysosomal cathepsins, the cytosolic calpains (which are calcium-activated) as well as several parasitic proteases (e.g those of *Trypanosoma schistosoma*). The X-ray structure of caspase-1 (also known as interleukin-1-beta converting enzyme) reveals a novel type of fold for cysteine proteases. Catalysis of the cysteine proteases proceeds through the formation of a covalent intermediate and involves a cysteine and a histidine residue (Cys25 and His159 under the papain numbering). The nucleophile is a thiolate ion, which is stabilized through the formation of an ion pair with the neighboring imidazolium group of His159. The attacking nucleophile is the thiolate-imidazolium ion pair in both steps.

The cysteine proteases are of great medical interest. Cysteine proteases in the papain family include mammalian enzymes such as cathepsins B and L, which are involved in cancer growth and metastasis, and cathepsin K, which is of importance for its involvement in bone degradation and osteoporosis. Other cysteine proteases are important enzymes for combating parasites because they are essential for the parasite-host interaction and are therefore attractive targets of inhibition such as cruzipain from *Trypanosoma cruzi*, which causes Chagas' disease, and falcipain from *Plasmodium falciparum*, which causes malaria. Other cysteine proteases such as those belonging to the legumain family, have been shown to play key roles in antigen presentation. Cysteine proteases of the caspase family are also of great interest as key mediators of apoptosis. Several cysteine proteases of pathogenic bacteria are virulence factors and cause severe problems for the host at infections, such as gingipains of *Porhyromonas gingivalis*, which is important in periodontitis, and streptopain from *Streptococcus pyogenes*.

Therefore, the cysteine proteases have been considered important targets for the identification of therapeutics.

SUMMARY OF THE INVENTION

The present invention provides compositions and methods for assessing profiles of one or more catalytically active enzymes in compositions comprising a plurality of proteins. In preferred embodiments, the enzyme(s) are one or more hydrolases, and in particularly preferred embodiments the hydrolase(s) are one or more cysteine proteases. The methods described herein use activity based probes ("ABPs") having an affinity moiety for directing the binding of the ABP(s) to one or more cysteine proteases, a reactive group for forming a covalent bond with the target enzyme(s) once the ABP has been bound, and a tag (e.g., a detectable label, preferably a fluorophore). One or more ABPs are combined with a protein-containing sample under conditions for binding and reaction of the ABP(s) with target enzymes that are present in the sample. In a preferred embodiment the reactive group reacts with an amino acid of the target enzyme to form a conjugate (i.e., a covalently linked ABP-target enzyme complex). The resulting products are then used to assess the active enzyme profile of the sample, and can be correlated to the presence, amount, or activity of one or more active target cysteine proteases, and/or other target enzymes, present in the original complex protein mixture.

By "hydrolase" is meant an enzyme that catalyzes the hydrolytic cleavage of covalent bonds. Such enzymes are classified by the IUPAC-IUBMB Joint Commission on Biochemical Nomenclature (www.chem.qmul.ac.uk/iupac/jcbn/) under the Enzyme Commission numbers EC 3.X. The terms "protease" and "proteolytic enzyme" as used herein refers to an enzyme that catalyzes the hydrolysis of peptide bonds in proteins and peptides.

The term "cysteine protease" as used herein refers to a proteolytic enzyme that utilizes a cysteine residue for catalytic activity. The nucleophile in the proteolytic reaction is a thiolate ion, which is stabilized through the formation of an ion pair with a imidazolium group of histidine, e.g., His159 in the case of papain. The attacking nucleophile is the thiolate-imidazolium ion pair in both steps. Papain is the archetype and the best studied member of the family.

Cysteine proteases include, but are not limited to, papain, caspases, and several cathepsins such as cathepsins B, H, L, K, O, S, T, V, and X, ananain, papain, chymopapain, and fruit bromelain. The caspases are also cysteine hydrolases. Caspase-1 is a cysteine hydrolase that is also known by several other names including interleukin 1β-converting enzyme, protease VII, protease A, interleukin 1β precursor protease, interleukin 1 converting enzyme, interleukin 1β-converting endopeptidase, interleukin-1β convertase, interleukin-1β converting enzyme, interleukin-1β precursor protease, prointerleukin 1β protease, precursor interleukin-1β converting enzyme, pro-interleukin 1β protease.

In a first aspect, the present invention relates to methods and compositions for determining an enzyme profile in a complex protein mixture. These methods comprise contacting the complex protein mixture with one or more distinct ABPs under conditions of reaction of the ABPs with the catalytically active target enzymes, preferably catalytically active hydrolases, and most preferably catalytically active cysteine proteases, whereby one or more conjugates of the ABP(s) and the active target enzymes(s) is (are) formed. In preferred embodiments each ABP specifically reacts with one or more catalytically active target enzyme(s), as defined hereinafter. Each ABP preferably comprises an affinity moiety conjugated to a TAG, such as a detectable label, and a reactive group that reacts with a target enzyme when the ABP binds to that target enzyme. The enzyme profile can then be analyzed by the screening and/or identification methods described hereinafter. Particularly preferred ABPs are also described hereinafter.

In preferred embodiments, the target enzymes are cysteine proteases such as caspases, or any of the cathepsins such as B, H, L, K, O, S, T, V, or X. Cathepsin L is a lysosomal cysteine protease whose overexpression in human melanoma cells increases their tumorigenicity and switches their phenotype from non-metastatic to highly metastatic. Cathepsin B, a lysosomal cysteine protease, is known to be involved in tumor progression and play an important role in the regulation of normal skeletal muscle cell differentiation. Cathepsin S is a lysosomal cysteine protease believed to have a role in numerous inflammatory diseases. Cathepsin K is a member of the papain family of cysteine proteases and is believed to have a role in bone degeneration in osteoporosis. Cathepsin V, a thymus and testis-specific cysteine protease, is believed to play a central role in the immune system and in cancer. D. Brömme, Z. Li, M. Barnes, E. Mehler (1999) "Human Cathepsin V: Functional Expression, Tissue Distribution, Electrostatic Surface Potential, Enzymatic Characterization, and Chromosomal Localization." *Biochemistry* 38: 2377-2385. The person of ordinary skill will realize that many cathepsins have been isolated, characterized, and their function determined. These other cathepsins are also contemplated as preferred target proteases in the present invention.

Apoptosis (also referred to as "programmed cell death") is triggered by a variety of stimuli, including ligand/receptor interactions (e.g., FAS receptor/FAS ligand), mitochondrial response to stress, and cytotoxic T cells. Caspases are a class of cysteine proteases that includes several representatives involved in apoptosis. The caspases convey the apoptotic signal in a proteolytic cascade, with caspases cleaving and activating other caspases that then degrade other cellular targets that lead to cell death. Caspases 1-10 have been identified, sequenced, and cloned. The caspases at the upper end of the cascade include caspase-8 and caspase-9. Caspase-8 is the initial caspase involved in response to receptors with a death domain like FAS. The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets. These and other caspases are also contemplated as preferred target proteases in the present invention.

In preferred embodiments, the ABP-enzyme conjugates can be separated from other components of the complex protein mixture, for example by sequestering one or more conjugates (e.g., by binding to a receptor that binds the tag portion of the ABP or by using a "tethered" ABP), by chromatographic methods, by mass spectrographic methods, and/or by other means such as electrophoresis.

In yet other embodiments, following reaction of the complex protein mixture with one or more ABPs, the resulting ABP-target enzyme conjugates may be proteolytically digested to provide ABP-labeled peptides. This digestion may occur while the conjugates are sequestered to a solid phase, or while free in solution. In preferred embodiments, one or more ABPs are selected such that each target enzyme forms a conjugate with a single ABP, most preferably at a single discrete location in the target enzyme; thus, each conjugate gives rise to a single ABP-labeled peptide. Enrichment, separation, or identification of one or more ABP-labeled peptides may be achieved using liquid chromatography and/or electrophoresis. Additionally, mass spectrometry may be employed to separate, fragment, and/or identify one or more ABP-labeled peptides by molecular weight and/or amino acid sequence. In particularly preferred embodiments, the sequence information derived from of the ABP-labeled peptide(s) is used to identify the enzyme from which the peptide originally derived. Variations of these aspects can involve the comparison of two or more proteomes, e.g., with ABPs having different tags, or, when analysis comprises mass spectrometry, having different isotopic compositions.

In preferred embodiments, ABP(s) and reaction conditions are selected such that the relative ability of a catalytically active target enzyme to become labeled depends on the relative level of catalytic activity of that target enzyme; the signal obtained from such labeling can be correlated to the catalytic activity of the target enzyme(s) in the proteomic mixture. Alternatively, ABP(s) can be used under conditions in which all catalytically active forms of one or more target enzymes are labeled, regardless of the level of catalytic activity of the particular target enzyme. For example, the time of reaction may be extended so that the labeling reaction goes substantially to completion; the signal obtained from such labeling will be unrelated to the relative catalytic activity of the various active target enzyme(s) in the proteomic mixture.

In yet another aspect, the instant invention relates to methods for comparing the presence, amount, and/or relative catalytic activity of one or more catalytically active target enzymes, preferably in two or more complex protein mixtures using the methods and compositions described herein. In various embodiments, these methods comprise one or more of the following steps: contacting one or more complex protein mixture(s) with one or more ABPs, where the ABP(s) specifically bind to one or more catalytically active target enzymes, preferably catalytically active target hydrolases, and most preferably catalytically active target cysteine proteases, present in each complex protein mixture; combining the complex protein mixtures following this contacting step to form a combined complex protein mixture; prior to and/or following this combination, removing one or more non-sequestered components of the complex protein mixture(s). The target enzyme profile can then be determined by analyzed by the screening and/or identification methods described hereinafter.

In preferred embodiments, the methods and compositions described herein are applied to determining the catalytically active target enzyme profiles, preferably catalytically active target hydrolase profiles, most preferably the catalytically active target cysteine protease profiles, of diseased tissue by obtaining one or more samples of diseased tissue to be examined, and determining the respective profile of the tissue sample using the methods and compositions described herein. In particularly preferred embodiments, the catalytically active target enzyme profile of the diseased tissue can be compared to that of normal samples to determine differences in the profiles of the two samples. In preferred embodiments the diseased tissue is a bone tissue sample, tumor tissue, or thymus tissue. In another embodiment the catalytically active target enzyme profile of target parasite organisms can be determined. For example, the catalytically active target cysteine protease profile of *Trypanosoma* or *Plasmodium* can be determined and used to provide information about how best to combat these parasites, whether in a living organism (such as a mammal or plant) or in the environment. Specific enzyme inhibitors can then be selected based on the profiles obtained.

In still another aspect, the present invention relates to methods and compositions for detecting disease in a test sample. In preferred embodiments the test sample will be a cell or tissue sample. In particularly preferred embodiments, the tissue sample will be a neoplasmic sample and the disease is a cancer. The methods involve determining the catalytically active target enzyme profile, preferably the catalytically active target hydrolase profile, and most preferably the catalytically active target cysteine protease profile, of the test sample; comparing the profile of the test sample with an appropriate profile of a known non-diseased sample and/or of a known diseased sample; and determining whether the test sample profile is indicative of the diseased state. A "non-diseased" sample is a sample of cells or tissues that is identified as not exhibiting a particular disease of interest. It is preferably a normal, healthy sample of the cells or tissue.

In another aspect the present invention provides methods of determining the inhibitory potency of a test compound against one or more catalytically active target enzymes. The methods involve contacting one or more ABPs with a test sample containing the test compound and the target enzyme(s); allowing the ABP(s) to react with target enzyme(s) contained in the test sample; and detecting a signal that indicates the ability of the ABP(s) to covalently bind to the target enzyme(s) in the test sample. In preferred embodiments, this ability to covalently bind is indicative of the level of activity of the target enzyme(s) in the test sample.

In preferred embodiments, this level of activity is compared to the level of activity of the target enzyme(s) in the absence of the test compound. By such methods, the inhibitory and/or stimulatory potency of the test compound against the target enzyme(s) can be determined. The "inhibitory potency" is the extent to which the presence of the compound causes the inhibition of target enzyme catalytic activity, while "stimulatory potency" is the extent to which the presence of the compound causes an increase in target enzyme catalytic activity.

In yet another aspect, the present invention provides kits for performing the methods described. The kits contain one or more of the materials described for conducting the methods. The kits can include one or more ABPs in the solid phase and/or in a liquid phase (such as buffers provided) in a package. The kits also can include buffers for preparing solutions for conducting the methods, and pipettes for transferring liquids from one container to another. By "package" is meant material enveloping a vessel containing the ABPs. In preferred embodiments, the package can be a box or wrapping. The kit can also contain items that are not contained within the package but are attached to the outside of the package, for example, pipettes.

The summary of the invention described above is not limiting and other features and advantages of the invention will be apparent from the following detailed description of the preferred embodiments, as well as from the claims.

DETAILED DESCRIPTION OF THE INVENTION

Figure 1:
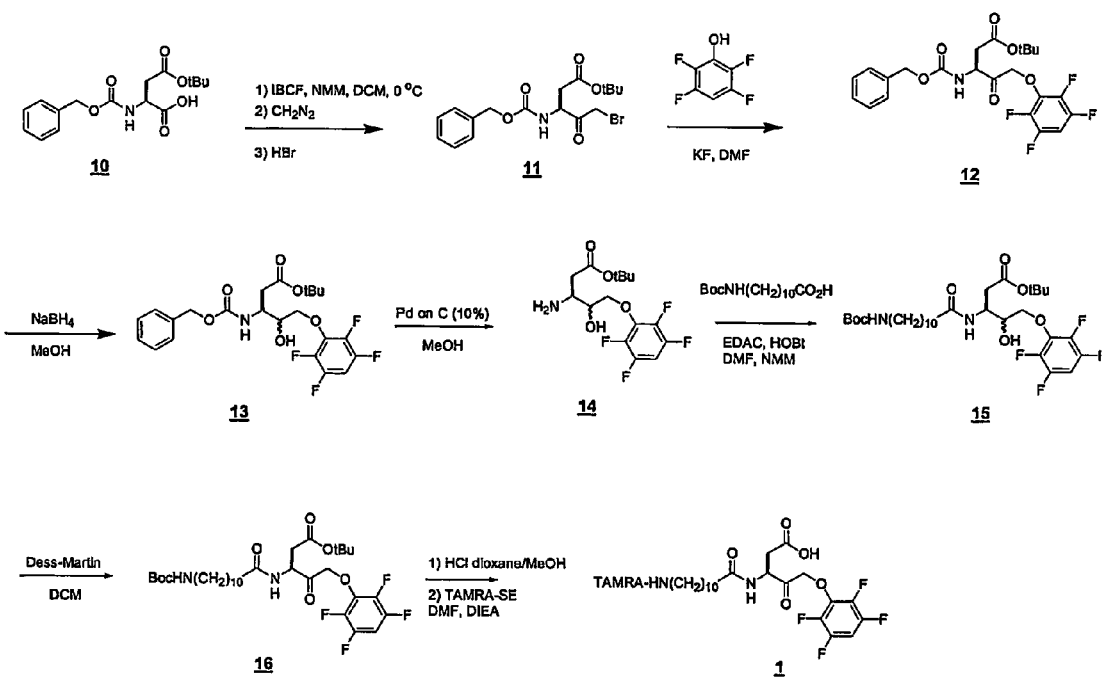
FIG. 1 provides an exemplary synthesis of an exemplary activity based probe of the present invention.

The subject methods and compositions can provide enhanced simplicity and accuracy in identifying changes in one or more enzymes present in of a complex protein mixture. These methods and compositions relate to activity based probes ("ABPs") that bind to catalytically active target enzymes, preferably catalytically active target hydrolases, and most preferably catalytically active target cysteine hydrolases. The profiling methods described herein can have a number of steps leading to the identification of catalytically active target enzymes in a complex protein mixture. A complex protein mixture, and preferably two or more complex protein mixtures, e.g., a sample and a control, can be used as obtained from a natural source or as processed, e.g., to remove interfering components and/or enrich the catalytically active target enzyme components. Each complex protein mixture to be analyzed is combined under reaction conditions with at least one ABP to produce conjugates with one or more catalytically active target enzyme(s). The ABPs used in two or more complex protein mixtures can differ as to the choice of tag moiety and/or isotopic composition in order for the labeled complex protein mixtures to be directly compared (e.g., in the same capillary of a capillary electrophoresis apparatus or lane in an electrophoresis gel, or in a mass spectrometer).

The analysis platforms described herein can differ as to the methods of enrichment and analysis using liquid chromatography and/or electrophoresis, and/or mass spectrometry for identification and quantitation. The choice of the platform is affected by the size of the sample, the rate of throughput of the samples, the mode of identification, and the need for and level of quantitation.

The compositions and methods described herein find use for the most part with biological samples, which may have been subject to processing before reaction with the ABPs. "biological sample" intends a sample obtained from a cell, tissue, or organism. Examples of biological samples include proteins obtained from cells (e.g., mammalian cells, bacterial cells, cultured cells, human cells, plant cells, etc.), particularly as a lysate, a biological fluid, such as blood, plasma, serum, urine, bile, saliva, tears, cerebrospinal fluid, aqueous or vitreous humor, or any bodily secretion), a transudate or exudate (e.g. fluid obtained from an abscess or other site of infection or inflammation), a fluid obtained from a joint (e.g. synnovial fluid obtained from a normal joint or a joint affected by disease such as rheumatoid arthritis, osteoarthritis, gout or septic arthritis), or the like.

Biological samples may be obtained from any organ or tissue (including a biopsy or autopsy specimen) or may comprise cells (including primary cells, passaged or cultured primary cells, cell lines, cells conditioned by a specific medium) or medium conditioned by cells. In preferred embodiments, a biological sample is free of intact cells. If desired, the biological sample may be subjected to prior processing, such as lysis, extraction, subcellular fractionation, and the like. See, Deutscher (ed.), 1990, Methods in Enzymology, vol. 182, pp. 147-238.

Of particular interest are samples that are "complex protein mixtures." As used herein, this phrase refers to protein mixtures having at least about 20, more usually at least about 50, preferably at least about 100 or more different proteins, where the particular distribution of proteins (or the activity thereof) is of interest. An example of such a complex protein mixture is a proteome, as defined hereinafter. Complex protein mixtures may be obtained from cells that are normal or abnormal in some particular, where the abnormality is informative as to treatment, status, disease, or the like, can be analyzed using the methods of the subject invention.

The term "proteome" as used herein refers to a complex protein mixture obtained from a biological sample. Preferred proteomes comprise at least about 5% of the total repertoire of proteins present in a biological sample (e.g., the cells, tissue, organ, or organism from which a lysate is obtained; the serum or plasma, etc.), preferably at least about 10%, more preferably at least about 25%, even more preferably about 75%, and generally 90% or more, up to and including the entire repertoire of proteins obtainable from the biological sample. Thus the proteome may be obtained from an intact cell, a lysate, a microsomal fraction, an organelle, a partially extracted lysate, biological fluid, a tissue, an organ, and the like. The proteome will be a mixture of proteins, generally having at least about 20 different proteins, usually at least about 50 different proteins and in most cases 100 different proteins or more.

Generally, the sample will have at least about $1 \times 10^{-11}$ g of protein, and may have 1 g of protein or more, preferably at a concentration in the range of about 0.1-50 mg/ml. For screening applications, the sample will typically be between about $1 \times 10^{-11}$ g of protein and about $1 \times 10^{-3}$ g of protein, preferably between about $1\times10^{-6}$ g of protein and $1\times10^{-4}$ g of protein. For identification of ABP-labeled target enzymes, the sample will typically be between about $1\times10^{-9}$ g of protein and about 1 g of protein, preferably between about $1\times10^{-4}$ g of protein and $1\times10^{-1}$ g of protein. The term "about" in this context refers to +/−10% of the amount listed.

The sample may be adjusted to the appropriate buffer concentration and pH, if desired. One or more ABPs may then be added, each at a concentration in the range of about 1 nM to 20 mM, preferably 10 nM to 1 mM, most preferably 10 nM to 100 µM. After incubating the reaction mixture, generally for a time for the reaction to go substantially to completion, generally for about 0.11-60 minutes, at a temperature in the range of about 5-40° C., preferably about 10° C. to about 30° C., most preferably about 20° C., the reaction may be quenched.

In one aspect of the invention, the method provides for quantitative measurement of catalytically active enzymes, preferably catalytically active hydrolases, and most preferably catalytically active target cysteine hydrolase, in biological fluids, cells or tissues. Moreover, the same general strategy can be broadened to achieve the proteome-wide, qualitative and quantitative analysis of the amount and/or activity of target enzymes, by employing ABPs with differing target specificities. The methods and compositions of this invention can be used to identify catalytically active target enzymes of low abundance that are present in complex protein mixtures and can be used to selectively analyze specific groups or classes of cysteine proteases, such as membrane or cell surface cysteine proteases, or cysteine proteases contained within organelles, sub-cellular fractions, or biochemical fractions such as immunoprecipitates. Further, these methods can be applied to analyze differences in expressed catalytically active target enzymes in different cell states. For example, the methods and reagents herein can be employed in diagnostic assays for the detection of the presence or the absence of one or more catalytically active cysteine proteases indicative of a disease state, such as cancer, bone degeneration or decalcification, or another disease state.

The subject methods can be used for a variety of purposes. The method can be used in the diagnosis of disease, the response of cells to an external agent, e.g. a drug, staging diseases, such as neoplasia, identifying cell differentiation and maturation, identifying new proteins, determining side effects of drugs, determining selectivity of drugs, identifying responses to drugs specific to certain genotypes (e.g., allelic differences in individuals), identifying useful ABPs from combinatorial libraries, etc.

In certain embodiments, the system uses ABPs specific for the catalytically active form of an enzyme or a group of enzymes, usually directed to an active site on such target enzymes, and combines one or a mixture of ABPs, depending on the specificity of the activity based ABPs and the variety in the group or groups of proteins to be assayed.

The term "activity based probes" ("ABPs") refer to molecules that specifically react with catalytically active target enzymes as compared to catalytically inactive enzymes. ABPs may be designed and synthesized using combinatorial chemistry and/or rational design methods. A detailed description of an ABP design strategy, in which a fluorescent moiety can act as a ligand, is provided in PCT Application No. PCT/US02/03808, entitled "Activity Based Probe Analysis", filed Feb. 5, 2002, PCT Application No. PCT/US00/34187, WO 01/7684, entitled "Proteomic Analysis," and PCT Application No. PCT/US00/34167, WO 01/7668, entitled "Proteomic Analysis," each of which is hereby incorporated by reference in its entirety, including all tables, figures, and claims. As described therein, goals of a design strategy are to provide ABPs that are able to react covalently with a targeted group of active proteins, while minimizing non-specific labeling.

Activity based probes may be present as a library, which refers to a plurality of such ABPs provided to analyze a particular individual sample. Such a library may be contacted with the sample simultaneously or in series, or the sample may be divided into individual aliquots for contacting with one or more members of the library. A library may also be present on one or more solid surfaces as "tethered" ABPs as described hereinafter.

In the present invention, it is not necessary that there be no reaction of an ABP with non-target proteins (or inactive target proteins). Rather, an ABP is defined as being "specific for," as "specifically reacting with," or as "specifically binding to," target enzymes(s) if the ABP provides at least about twice the amount of signal from ABP labeling of target enzymes (preferably catalytically active target cysteine proteases) when compared to an equivalent amount of non-target (or catalytically inactive) target protein. Preferably the signal obtained from target enzyme(s) will be at least about five fold, preferably 10 fold, more preferably 25-fold, even more preferably 50-fold, and most preferably 100-fold or more, greater than that obtained from an equivalent amount of non-target (or inactive) protein.

The term "target enzyme" as used herein refers to an enzyme, an active site of which becomes labeled by one or more ABPs when the ABP(s) binds to the target enzyme(s). The cysteine proteases are preferred target enzymes, particularly those classified under the Enzyme Commission number 3.4.22. ABP(s) may be provided that are specific for catalytically active cysteine proteases, in that catalytically active enzymes that are not cysteine proteases do not specifically react with the ABPs. Alternatively, ABP(s) may be provided that have broader reactivity, in that they specifically react with catalytically active cysteine proteases, but also react with other catalytically active enzymes, such as other hydrolases. Particularly preferred target cysteine proteases include caspase and the cathepsins, such as cathepsins B, L, K, S, T, or X.

The terms "catalytically active target enzyme," "catalytically active target hydrolase" or "catalytically active target cysteine protease" each refer to a target enzyme, hydrolase, or cysteine protease that is in its native conformation and is able to interact with an entity with which it normally interacts, e.g. enzyme with substrate and/or cofactor, etc., in order to carry out its catalytic function.

The term "inactivated" as used herein refers to a sample that has been treated so that at least a portion of target enzymes that were catalytically active in the original sample are rendered inactive. An "inactive enzyme" can result from various mechanisms such as denaturation, inhibitor binding, either covalently or non-covalently, mutation, secondary processing, e.g. phosphorylation or dephosphorylation, etc. Functional states of enzymes, such as hydrolases or cysteine proteases, as described herein may be distinct from the level of abundance of the same enzymes. Inactivated samples may be used to validate the activity-specific binding of ABPs as described herein.

The term "untreated" as used herein refers to a sample that has not been exposed to one or more conditions as compared to a second sample not exposed to such conditions. An untreated sample may be a sample that has not been inactivated; alternatively, an untreated sample may be one not exposed to one or more molecules (e.g., drug lead compounds) in a screening assay. Thus the compositions and methods described herein may be used to compare a complex protein mixture obtained from cell(s), tissue(s), or organism(s) treated with one or more compounds (e.g., lead compounds in drug discovery) to a complex protein mixture obtained from cell(s), tissue(s), or organism(s) not so treated. ABP-labeled proteins and/or peptides from the two samples may be compared for relative signal intensity. Such methods may indicate alterations in active protein content due to the treatment regimen. Additionally, such methods can also differentiate between treatments that act by direct inhibition of specific proteins ("primary effects") versus treatments that affect active protein content upstream, e.g., by altering expression of protein(s) ("secondary effects").

An "active site" of a protein refers to an area on the surface of a protein, e.g., an enzyme molecule or surface membrane receptor, to which a binding molecule, e.g. substrate or reciprocal ligand, is bound and results in a change in the protein, substrate, and/or ligand. For a receptor, the conformation may change, the protein may become susceptible to phosphorylation or dephosphorylation or other processing, etc. For the most part, the active site will be the site(s) of an enzyme where the substrate and/or a cofactor bind, where the substrate and cofactor undergo a catalytic reaction; where two proteins form a complex, e.g. the site at which a G protein binds to a surface membrane receptor, two Kringle structures bind, sites at which transcription factors bind to other proteins; or sites at which proteins bind to specific nucleic acid sequences, etc.

In referring to affinity for an ABP to a target enzyme, one is concerned with the on-rate of the ABP with the target enzyme(s), since there is a negligible off-rate, where the ABP covalently bonds to the target enzyme. One can determine relative on-rates between ABPs by having less than a stoichiometric amount of the target enzyme as compared to the total amount of one or more ABPs and then measuring the relative amounts of the conjugates for each of the ABPs. In this way one can obtain a measure of the relative activity of each of the ABPs toward the active target protease, which for the purposes of this invention may be considered the affinity, if not the binding affinity, of the ABPs for the target protease.

Structure of Activity Based Probes

The activity based probes of the present invention comprise a warhead linked to a tag by a linker moiety. As will be described hereinafter, each of the warhead, the linker moiety ("L"), and the tag ("TAG") may be independently selected to provide different target enzyme specificities. Each of these components of an ABP is described in additional detail below. In preferred embodiments the present invention provides ABPs for detecting and/or measuring the catalytically active cysteine proteases in a sample.

Particularly preferred ABPs have the structure:

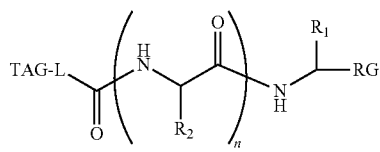

wherein each $R_1$ and $R_2$ is independently hydrogen or an alkyl, alkenyl, alkynl, aryl, heteroaryl or alkylaryl group, optionally containing one or more heteroatoms selected from the group consisting of N, O, or S;
RG is a reactive group capable of covalently binding to a catalytically active target enzyme, preferably comprising a leaving group "LG" that is lost upon formation of a covalent bond between the ABP and the target enzyme;
TAG is a detectable label;
L is a linker moiety;

n is an integer of from 0 to 4;
or a pharmaceutically acceptable salt or complex thereof.

$R_1$ and $R_2$ can be independently hydrogen or any alkyl, alkenyl, alkynl, aryl, or alkylaryl group, optionally containing one or more heteroatoms selected from the group consisting of N, O, or S. In various embodiments $R_1$ and $R_2$ will have from 1 to 100 atoms, 1 to 50 atoms, or 1 to 20 atoms. Most preferably, $R_1$ and $R_2$ will have from about 1 to 60 atoms, usually 1 to 30 atoms, where the atoms include C, N, O, S, P, etc., particularly C, N and O, and will generally have from about 1 to 12 carbon atoms and from about 0 to 8, usually 0 to 6 heteroatoms. The number of atoms referred to above are exclusive of hydrogen in referring to the number of atoms in a group, unless indicated otherwise. $R_1$ and $R_2$ are preferably independently hydrogen or $C_{1-6}$ alkyl, straight or branched chain, optionally containing from 1-3 heteroatoms selected from the group consisting of N, O, or S; or $C_{0-6}$ alkyl aryl, $C_{0-6}$ alkyl heteroaryl, or $C_{0-6}$ alkyl phenyl. Most preferably, $R_1$ and $R_2$ are independently selected from the side chains of the 20 common α-amino acids:

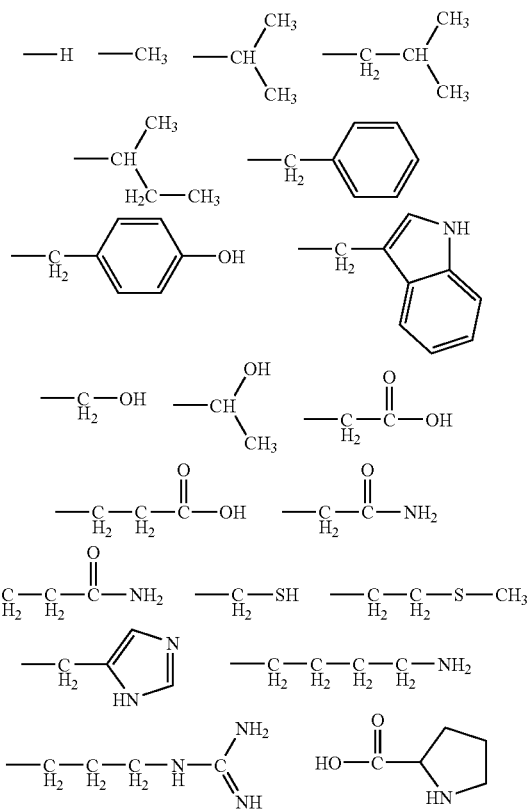

note: because proline comprises a fused side chain and main chain, the entire structure and not just the side chain is shown.

TAG is preferably a fluorophore and most preferably the fluorophore is a rhodamine such as TAMRA, or other fluorescent dye, but the person of ordinary skill will realize that any detectable tag (including other fluorophores) that permits the chemical reaction to proceed and provides a signal will function in the invention.

L is preferably an alkyl or heteroalkyl chain of 1-20 backbone atoms selected from —N(R)—, —O—, —S— or —C(R)(R)—, where each R is independently H or a —$C_{1-6}$ alkyl straight or branched chain. The linker moiety L preferably has 10 carbons, and most preferably is a hydrocarbon chain of about 10 carbons. The linker moiety can also contain atoms other than carbon such as, for example, oxygen, nitrogen, phosphorus, or sulfur. Particularly preferred linkers L are polyoxyalkylene (e.g., polyoxyethylene: —CH$_2$—CH$_2$—O—) chains of from 1 to 5 oxyalkylene groups. The person of ordinary skill will realize the linker moiety can have many embodiments, as long as the ABP is able to bring the reactive group in proximity with a reactive chemical group on the target enzyme for reaction and formation of a covalent bond.

In the most preferred embodiments, n=0 or 1.

The term "warhead" as used herein refers to the portion of an ABP that is directed to and binds with an active site of a target enzyme. The warhead comprises a reactive group ("RG") and an affinity moiety ("R"). Affinity moiety (R) refers to a chemical group, which may be a single atom, that is conjugated to the reactive group or associated with the linker moiety that provides enhanced binding affinity for protein targets and/or changes the binding profile of the warhead. The affinity moiety is preferably less than 1 kilodalton in mass.

The reactive group RG can be any group capable of covalently bonding to a target enzyme when the ABP is bound to the target enzyme. Preferably, RG comprises a leaving group "LG" that is lost upon formation of a covalent bond between the ABP and the target

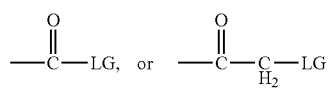

enzyme. Most preferably the reactive group RG is a phenoxy or benzyloxy derivative. In various preferred embodiments the reactive group RG can be one of the following structures:

where LG has one of the following structures:

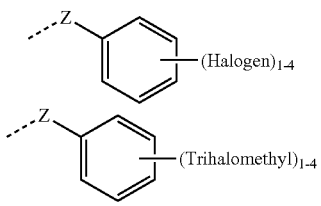

wherein Z is O or

and most preferably is selected from the following group:

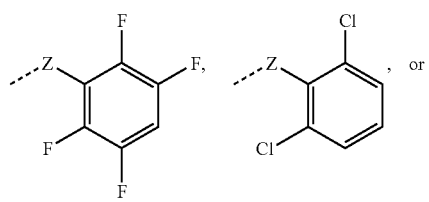

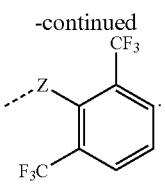

Exemplary RGs as used in an ABP of the invention include phenoxy and benzyloxy methyl ketone derivatives, alpha-haloketones, and aryl thiol methyl ketones.

The term "linker moiety" refers to a bond or chain of atoms used to link one moiety to another, serving as a covalent linkage between two or more moieties. Since in many cases, the synthetic strategy will be able to include a functionalized site for linking, the functionality can be taken advantage of in choosing the linking moiety. The choice of linker moiety has been shown to alter the specificity and/or the physical characteristics (e.g., solubility) of an ABP. See, e.g., Kidd et al., *Biochemistry* (2001) 40: 4005-15. For example, an alkylene linker moiety and a linker moiety comprising a repeating oxyalkylene structure (polyethylene glycols, or "PEG"), have distinct specificities and provide distinct protein profiles. Thus, one of skill in the art can select the linker moiety of the ABP in order to provide additional specificity of the ABP for a particular protein or protein class.

Linker moieties include among others, ethers, polyethers, diamines, ether diamines, polyether diamines, amides, polyamides, polythioethers, disulfides, silyl ethers, alkyl or alkenyl chains (straight chain or branched and portions of which may be cyclic) aryl, diaryl or alkyl-aryl groups, having from 0 to 3 sites of aliphatic unsaturation. While normally amino acids and oligopeptides are not preferred, when used they will normally employ amino acids of from 2-3 carbon atoms, i.e. glycine and alanine. Aryl groups in linker moieties can contain one or more heteroatoms (e.g., N, O or S atoms). The linker moieties, when other than a bond, will have from about 1 to 60 atoms, usually 1 to 30 atoms, where the atoms include C, N, O, S, P, etc., particularly C, N and O, and will generally have from about 1 to 12 carbon atoms and from about 0 to 8, usually 0 to 6 heteroatoms. The number of atoms referred to above are exclusive of hydrogen in referring to the number of atoms in a group, unless indicated otherwise.

Linker moieties may be varied widely depending on their function, including alkyleneoxy and polyalkyleneoxy groups, where alkylene is of from 2-3 carbon atoms, methylene and polymethylene, polyamide, polyester, and the like, where individual monomers will generally be of from 1 to 6, more usually 1 to 4 carbon atoms. The oligomers will generally have from about 1 to 10, more usually 1 to 8 monomeric units. The monomeric units may be amino acids, both naturally occurring and synthetic, oligonucleotides, both naturally occurring and synthetic, condensation polymer monomeric units and combinations thereof.

The term "TAG" as used herein refers to a molecule that can be used to detect and/or capture the ABP in combination with any other moieties that are bound strongly to the TAG, so as to be retained in the process of the reaction of the reactive moiety of the ABP with the target protease. The TAG may be added to the warhead-linker moiety combination after reaction with the target enzyme, to form the complete ABP. For this purpose, the warhead-linker moiety combination will include a chemically reactive moiety, normally not found in proteins, that will react with a reciprocal functionality on the TAG, e.g., vicinal-diols with boronic acid, photoactivated groups, such as diazo bisulfites, azide with an alkene or alkyne, o-alkyl hydroxylamine with a ketone or aldehyde, etc. The warhead-linker moiety is then reacted with the TAG to complete the ABP. The TAG portion permits capture of the conjugate of the target enzyme and the ABP. The TAG may be displaced from the capture reagent by addition of a displacing TAG, which may be free TAG or a derivative of the TAG, or by changing solvent (e.g., solvent type or pH) or temperature or the linker may be cleaved chemically, enzymatically, thermally or photochemically to release the isolated materials (see discussion of the linker moiety, below).

Examples of TAGs include, but are not limited to, detectable labels such as fluorescent moieties and electrochemical labels, biotin, digoxigenin, maltose, oligohistidine, 2,4-dinitrobenzene, phenylarsenate; ssDNA, dsDNA, a polypeptide, a metal chelate, and/or a saccharide. Examples of tags and their capture reagents also include but are not limited to: dethiobiotin or structurally modified biotin-based reagents, including deiminobiotin, which bind to proteins of the avidin/streptavidin family, which may, for example, be used in the forms of strepavidin-Agarose, oligomeric-avidin-Agarose, or monomeric-avidin-Agarose; any vicinal diols, such as 1,2-dihydroxyethane ($HO-CH_2-CH_2-OH$), and other 1,2-dihyroxyalkanes including those of cyclic alkanes, e.g., 1,2-dihydroxycyclohexane which bind to an alkyl or aryl boronic acid or boronic acid esters, such as phenyl-$B(OH)_2$ or hexyl-$B(OEthyl)_2$ which may be attached via the alkyl or aryl group to a solid support material, such as Agarose; maltose which binds to maltose binding protein (as well as any other sugar/sugar binding protein pair or more generally to any tag/tag binding protein pairs that has properties discussed above); a hapten, such as the dinitrophenyl group, to which an antibody can be generated; a tag which binds to a transition metal, for example, an oligomeric histidine will bind to Ni(II), the transition metal capture reagent may be used in the form of a resin bound chelated transition metal, such as nitrilotriacetic acid-chelated Ni(II) or iminodiacetic acid-chelated Ni(II); glutathione which binds to glutathione-S-transferase. For the most part, the TAGs will be haptens that bind to a naturally occurring receptor, e.g. biotin and avidin, or an antibody or will be a detectable label, that is also a hapten.

One may use chemical affinity resins, e.g. metal chelates, to allow for digestion of proteins on the solid phase resin and facilitate automation. One example of this is the use of immobilized nickel (II) chelates to purify peptides that have six consecutive histidine residues (His-6 tag) (as described in the Invitrogen product brochure ProBond™ Resin (Purification) Catalog nos. R801-01, R801-15 Version D 000913 28-0076), which could be adapted to include non-peptidic chemical linkage coupling a series of imidazole-containing moieties. Alternative chemical attachments include phenyldiboronic acids (described in Bergseid, M. et al. Biotechniques (2000) 29(5), 1126-1133), and disulfide reagents (described in Daniel, S M et al., Biotechniques (1998) 24(3), 484-489). Additionally, chemical affinity tags that are useful in combinatorial synthesis could be adapted for modified peptide purification (reviewed in Porco, JA (2000) Comb. Chem. High Throughput Screening 3(2) 93-102

The term "fluorescent moiety" ("F1") refers to a TAG that can be excited by electromagnetic radiation, and that emits electromagnetic radiation in response in an amount sufficient to be detected in an assay. The skilled artisan will understand that a fluorescent moiety absorbs and emits over a number of wavelengths, referred to as an "absorbance spectrum" and an "emission spectrum." A fluorescent moiety will exhibit a peak emission wavelength that is a longer wavelength than its peak absorbance wavelength. The term "peak" refers to the highest point in the absorbance or emission spectrum.

The fluorescent moiety F1 may be varied widely depending upon the protocol to be used, the number of different ABPs employed in the same assay, whether a single or plurality of lanes are used in the electrophoresis, the availability of excitation and detection devices, and the like. For the most part, the fluorescent moieties that are employed as TAGs will absorb in the ultraviolet, infrared, and/or most preferably in the visible range and emit in the ultraviolet, infrared, and/or most preferably in the visible range. Absorption will generally be in the range of about 250 to 750 nm and emission will generally be in the range of about 350 to 800 nm. Illustrative fluorescent moieties include xanthene dyes, naphthylamine dyes, coumarins, cyanine dyes and metal chelate dyes, such as fluorescein, rhodamine, rosamine, the BODIPY dyes (FL, TMR, and TR), dansyl, lanthanide cryptates, erbium, terbium and ruthenium chelates, e.g. squarates, and the like. Additionally, in certain embodiments, one or more fluorescent moieties can be energy transfer dyes such as those described in Waggoner et al., U.S. Pat. No. 6,008,373. The literature amply describes methods for linking fluorescent moieties through a wide variety of linker moieties to other groups. The fluorescent moieties that find use will normally be under 2 kDal, usually under 1 kDal.

Preferred fluorescent moieties F1 can include elaborated conjugated pyran molecules, including xanthenes. Such molecules include eosin, erythrosin, fluorescein, Oregon green, and various commercially available Alexa Fluor® dyes (Molecular Probes, Inc.). Structural examples of such dyes include:

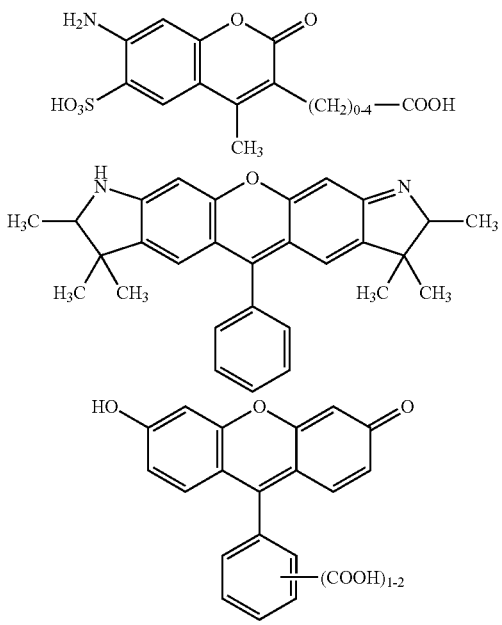

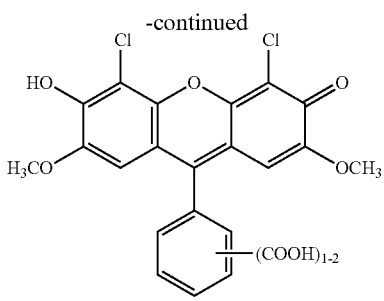

Particularly preferred fluorescent moieties are the rhodamine dyes. These molecules typically have the general structure:

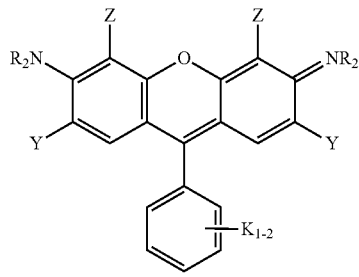

where K is —CO$_2$H, or —SO$_3$H; Y is —H, —CH$_3$, or together with R forms a six-membered ring; Z is —H or together with R forms a six-membered ring; and R is —H, —CH$_3$, —CH$_2$CH$_3$, or together with Y or Z forms a six-membered ring. Rhodamine molecules such as tetramethylrhodamine, 5-carboxytetramethylrhodamine, 6-carboxytetramethylrhodamine, carboxyrhodamine-6G, rhodamine-B sulfonyl chloride, rhodamine-red-X, and carboxy-X-rhodamine are well known to those of skill in the art. See, e.g., Handbook of Fluorescent Probes and Research Products, Molecular Probes, Inc., 2001, which is hereby incorporated by reference in its entirety. Advantageous properties of rhodamines include high quantum yields, low sensitivity of fluorescence over a pH range of from about pH 3 to about pH 8, advantageous water solubility, good photostability, and absorption of light in the visible spectrum. Particularly preferred fluorescers are 5-carboxytetramethylrhodamine and 6-carboxytetramethylrhodamine.

Other preferred fluorescent moieties F1 include the BODIPY dyes, which are elaborations of a 4-bora-3a,4a-diaza-s-indacene structure. Exemplary structures are provided below:

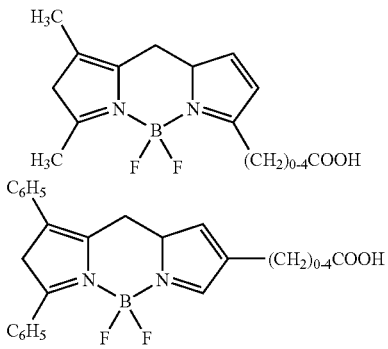

Yet other preferred fluorescent moieties include the cyanine dyes, conjugated structures comprising a polymethine chain terminating in nitrogen atoms. Typically, the nitrogens are themselves part of a conjugated heterocycle. An exemplary structures is

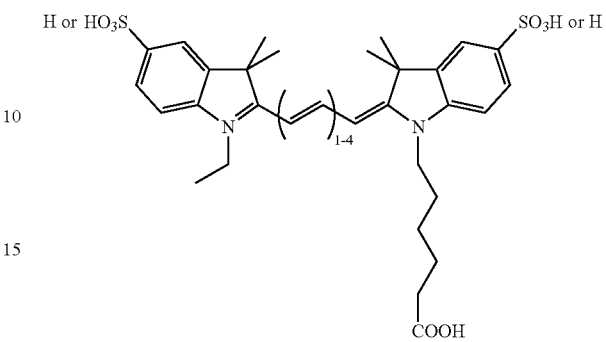

provided below:

Also of interest for use as TAGs are matched dyes as described in U.S. Pat. No. 6,127,134, which is hereby incorporated by reference in its entirety, including all tables, figures, and claims, which is concerned with labeling proteins with dyes that have different emissions, but have little or no effect on relative migration of labeled proteins in an electrophoretic separation. Of particular interest are the cyanine dyes disclosed therein, being selected in '134 because of their positive charge, which matches the lysine to which the cyanine dyes bind. In addition there is the opportunity to vary the polyene spacer between cyclic ends, while keeping the molecular weight about the same with the introduction of an alkyl group in the shorter polyene chain dye to offset the longer polyene. Also described are the BODIPY dyes, which lack a charge. The advantage of having two dyes that similarly affect the migration of the protein would be present when comparing the native and inactivated samples, although this would require that in the inactivated sample at least a portion of the protein is monosubstituted.

In each of the foregoing examples of preferred TAGs, carboxyl groups can provide convenient attachment sites for linker moieties. In the particularly preferred 5- and 6-carboxyrhodamine molecules, the 5- or 6-carboxyl is particularly preferred as an attachment site:

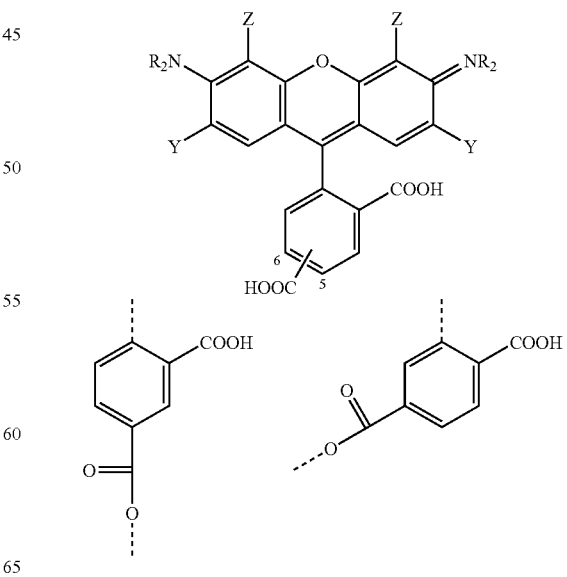

In general, any affinity label-capture reagent commonly used for affinity enrichment, which meets the suitability criteria discussed above, can be used in the method of the invention. Biotin and biotin-based affinity tags are particularly preferred. Of particular interest are structurally modified biotins, such as deiminobiotin or dethiobiotin, which will elute from avidin or streptavidin (strept/avidin) columns with biotin or under solvent conditions compatible with ESI-MS analysis, such as dilute acids containing 10-20% organic solvent. For example, deiminobiotin tagged compounds will elute in solvents below about pH4.

In certain embodiments, one or more ABPs can be immobilized on a solid phase to form "tethered" ABP(s). Exemplary compositions and methods useful for providing tethered ABPs are described in U.S. Provisional Application No. 60/363,762, entitled "Tethered Activity-Based Probes and Uses Thereof," which is hereby incorporated by reference in its entirety. In preferred embodiments, a plurality of different ABPs may be tethered to different regions of one or more solid phases to form a patterned array. Such a patterned array having two or more regions comprising ABPs that differ in structure and/or reactivities from each other could be used to simultaneously measure the presence, amount, or activity of a plurality of catalytically active target enzymes. The term "solid phase" as used herein refers to a wide variety of materials including solids, semi-solids, gels, films, membranes, meshes, felts, composites, particles, and the like typically used by those of skill in the art to sequester molecules. The solid phase can be non-porous or porous. Suitable solid phases include those developed and/or used as solid phases in solid phase binding assays. See, e.g., chapter 9 of *Immunoassay*, E. P. Diamandis and T. K. Christopoulos eds., Academic Press: New York, 1996, hereby incorporated by reference. Examples of suitable solid phases include membrane filters, cellulose-based papers, beads (including polymeric, latex, glass, and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997 (1998); Kessler et al., Agnew. Chem. Int. Ed. 40: 165 (2001); Smith et al., J. Comb. Med. 1: 326 (1999); Orain et al., Tetrahedron Lett. 42: 515 (2001); Papanikos et al., J. Am. Chem. Soc. 123: 2176 (2001); Gottschling et al., Bioorg. And Medicinal Chem. Lett. 11: 2997 (2001).

The ABP(s) employed will have an affinity for an active site, which may be specific for a particular active site or generally shared by a plurality of related proteins. The affinity may be affected by the choice of the reactive group, the linker moiety, the binding moiety, the TAG, or a combination thereof. One or more ABP(s) may be designed that exhibit specificity for a single target enzyme, or that exhibit specificity for a plurality of targets that may be structurally or functionally related.

Therefore, the present invention provides compositions and methods for the comparative quantification of differentially expressed proteins. The present invention enables one to directly monitor the functional state of large enzyme families, such as cysteine proteases. The ABPs of the present invention are able to 1) directly react with a broad range of catalytically active enzymes present in a complex proteome, preferably with one or more catalytically active hydrolases, more preferably one or more catalytically active cysteine hydrolases; 2) display minimal reactivity with non-target proteins; and 4) possess a TAG for the rapid detection and isolation of ABP reaction products. Thus, the present invention provides methods of comparatively measuring and identifying the active members of a given enzyme class present in two or more proteomes.

The following examples are offered by way of illustration and not by way of limitation.

Example 1

Manufacture of Caspase-Related Probes

The following examples illustrate some embodiments of methods for manufacturing the ABPs of the present invention. In each of these embodiments, $^1$H-NMR spectra were recorded using deuterated chloroform (CDCl$_3$; δ=7.26 ppm) as the solvent (unless otherwise indicated). Preparative HPLC was carried out on a reverse phase Polaris C18 column (5 μm column; 150 mm×21 mm; Metachem/Ansys; Torrance, Calif.) using a binary system of water and acetonitrile with trifluoroacetate as a modifier (water 0.1%, acetonitrile 0.08%). Analytical LC-MS was carried out on a Polaris C18 column (5μ column; 50 mm×4.6 mm; Metachem/Ansys; Torrance, Calif.) using a binary system of water and acetonitrile with TFA as a modifier (water 0.025%, acetonitrile 0.02%). The detectable TAGs were the mixed succinimidyl esters of 5-(and 6)-carboxytetramethylrhodamine (TAMRA-SE; Molecular Probes; Eugene, Oreg.), Boc-11-aminoundecanoic acid, and Cbz-Asp(OtBut)-OH (Calbiochem-Novachem Corp., La Jolla, Calif.).

3-Benzyoxycarbonylamino-5-bromo-4-oxo-pentanoic acid tert-butyl ester (11)

A dry round bottom flask was equipped with a magnetic stir bar and charged with dry THF and nitrogen gas. Cbz-Asp (OtBut)-OH (Composition 10, 1.0 g, 3.09 mmol) and N-methylmorpholine (0.5 mL, 4.6 mmol, 1.5 eqiv.) were dissolved in this mixture and the resulting solution was cooled to 0° C. in a water-ice bath. Isobutyl chloroformate (0.47 mL, 3.7 mmol, 1.2 eqiv.) was added with constant stirring and dropwise over a 10 minute period. The reaction was allowed to stir for 15 minutes at 0° C. In a separate reaction flask equipped with a magnetic stir bar was prepared a biphasic mixture of 10 N KOH and ethyl ether cooled in an ice bath. 1-methyl-3-nitro-1-nitrosquanidine (0.54 g, 3.7 mmol, 3 eqiv) was added slowly with constant stirring to give a bright yellow ethereal layer, which was then transferred into the flask containing Composition 10 via a plastic pipette. The resulting solution was stirred for 15 minutes at 0° C. and a concentrated solution of HBr (1 mL) was added dropwise. The reaction was stirred for an additional 20 minutes. To the clear biphasic mixture was added EtOAc (100 mL) and the organic layer was washed with H$_2$O (100 mL), saturated NaHCO$_3$ solution (100 mL), and dried over Na$_2$SO and concentrated in vacuo. Purification via column chromatography (silica gel, 2:1, hexanes/EtOAc) yielded 11 (0.62 g, 1.55 mmol, 51% yield) as a clear colorless oil. ESMS: 344.2 (M+H$^+$), 366.2 (M+Na$^+$).

3-Benzyloxycarbonylamino-4-oxo-5-(2-,3,5,6-tetrafluoro-phenoxy)-pentanoic acid tert-butyl ester (12)

2,3,5,6-tetrafluorophenol (150 mg, 0.90 mmol, 1.05 eq.) and KF (100 mg, 1.78 mmol, 2 eq.) in DMF (3 mL) were added to a dry round bottom flask equipped with a magnetic stir bar. Composition 11 (353 mg, 0.88 mmol) was added to the solution and the reaction was stirred overnight (12 h). Saturated NaHCO$_3$ solution (~50 mL) was added to the completed reaction and the aqueous layer extracted with EtOAc (2×50 mL). The organic layers were combined and washed with saturated brine solution (50 mL), dried over Na$_2$SO$_4$ and concentrated in vacuo to give a clear oil. Purification via column chromatography (silica gel, 2:1 hexanes/EtOAc) yielded 12 as a sticky off-white solid (186 mg, 0.36 mmol, 42% yield) ESMS: 486.4 (M+H$^+$), 509.6 (M+Na$^+$).

3-Benzyloxycarbonylamino-hydroxy-5-(2,3,5,6-tetrafluoro-phenoxy)-pentanoic acid tert-butyl ester (13)

To a dry round bottom flask equipped with a magnetic stir bar was added composition 12 (189 mg, 0.38 mM, 1 equiv) and MeOH (20 mL). With constant stirring was added NaBH$_4$ (8 mg, 0.228 mmol, 0.6 equiv). Upon addition gas bubbles were produced and the resulting clear colorless solution was stirred at 0° C. for 30 minutes. Solvent was removed in vacuo and the resulting solid was purified via column chromatography (silica gel, 2:1, hexanes/EtOAc) to give 13 as a sticky white solid. (165 mg, 0.34 mmol, 81% yield) ESMS: 488.2 (M+H$^+$), 510.8 (M+Na$^+$).

3-Amino-4-hydroxy-5-(2,3,5,6-tetrafluoro-phenoxy)-pentanoic acid tert-butyl ester (14)

Composition 13 (163 mg, 0.33 mmol) and MeOH (~15 mL) was added to a dry round bottom flask equipped with a magnetic stir bar. The flask was purged several times with N$_2$ and a catalytic amount of 10% Pd on C was carefully added to the reaction flask. The resulting black heterogeneous mixture was evacuated under vacuum and charged twice with H$_2$ via a rubber balloon with constant stirring. The reaction was stirred at room temperature for 1.5 h and upon completion was filtered thru a pad of Celite, concentrated in vacuo to give 14 (115 mg, 0.32 mmol, 99% yield) as a sticky off-white solid. ESMS: 354.8 (M+H), 376.2 (M+Na$^+$).

3-(11-tert-Butoxycarbonylamino-undecanoylamino)-4-hydroxy-5-(2,3,5,6-tetrafluoro-phenoxy)-pentanoic acid tert-butyl ester (15)

Boc-11-amino-undecanoic acid (115 mg, 0.38 mmol, 1.2 equiv), EDAC (91 mg, 0.48 mmol, 1.5 equiv), and HOBt (65 mg, 0.48 mmol, 1.5 equiv) in DMF (10 mL) were added to a dry round bottom flask equipped with a magnetic stir bar. Composition 14 (115 mg, 0.32 mmol) and N-methylmorpholine (twice distilled, 0.14 mL, 0.96 mmol, 3.0 equiv) dissolved in minimal quantity of DMF were added with constant stirring. The colorless solution slowly turned yellow as the reaction proceeded. The reaction was allowed to stir for 18 h, then EtOAc (20 mL) was added and the organic layer was washed with saturated NaHCO$_3$ (20 mL), H$_2$O (20 mL) and brine (20 mL), dried over Na$_2$SO$_4$, and concentrated in vacuo. The resulting oil was purified via column chromatography (silica gel, 1:1, hexane/EtOAc) to give 15 (56 mg, 0.088 mmol, 24% yield) as a clear, thick oil. ESMS: 637.6 (M+H), 659.2 (M+Na$^+$).

3-(11-tert-Butoxycarbonylamino-undecanoylamino)-4-oxo-5-(2,3,5,6-tetrafluoro-phenoxy)-pentanoic acid tert-butyl ester (16)

Composition 15 (56 mg, 0.088 mmol) and Dess-Martin periodinane (48 mg, 0.114 mmol, 1.3 equiv) in DCM (2 mL) were added to a dry round bottom flask equipped with a magnetic stir bar. The cloudy white suspension was allowed to react for 20 minutes. Saturated NaHCO$_3$ (20 ml) was added and the reaction was extracted with EtOAc (20 mL). The organic layer was dried over NaHCO$_3$, concentrated in vacuo, and purified via column chromatography (silica gel, 1:1, hexanes/EtOAc) to give 16 (23 mg, 0.036 mmol, 64% yield) as a sticky white solid. ESMS: 635.4 (M+H$^+$), 657.2 (M+Na$^+$).

[9-(2-Carboxy 4-{10,[1-carboxymethyl-2-oxo-3-(2,3,5,6-tetrafluoro-phenoxy)-propylcarbamoylamino-xanthen-3-ylidene]-dimethyl-ammonium (1)

Composition 16 (14 mg, 0.022 mmol) in 4 M HCl/dioxane (2 mL) was added to a dry round bottom flask equipped with a magnetic stir bar. To this solution was added dry MeOH (0.2 mL) and the resulting clear solution was allowed to stir at room temperature for 30 minutes after which the solvent was removed in vacuo. The resulting solid was taken up in a minimal amount of DMF and then added slowly dropwise to TAMRA-SE (14 mg, 0.026 mmol, 1.2 equiv) and DIEA (8 μL, 0.044 mmol, 2.0 equiv) in DMF (~0.2 mL) at room temperature. After 20 minutes the reaction was diluted with TFA (0.3 mL) to remove any intermediates containing tert-butyl ester protecting groups. The reaction solution was then diluted with DMSO (1.5 mL) and purified using preparative HPLC at a flow rate of 30 mL/minute and a 90 minute gradient of 0.1% TFA/acetonitrile:0.1% TFA/water (2-98%) to yield 1 as a bright purple solid (6 mg, 0.0067 mmol, 31% yield). $^1$H NMR(CD$_3$OD) δ 8.76 (s, 2H) 8.43 (d, 1H, J=9.6 Hz), 8.25 (d, 2H, J=9.5 Hz), 8.18 (d, 1H, J=9.8 Hz), 7.82 (s, 1H), 7.52 (d, 2H, J=8 Hz), 7.14 (d, 4H, J=9.8 Hz), 7.06 (d, 4H, J=9.7 Hz), 6.98 (d, 6H, J=2.4H), 5.18 (m, 4H), 4.78 (m, 2H), 4.34 (m, 4H), 3.46 (m, 4H), 3.38 (m, 3H), 2.88 (m, 2H), 2.73 (m, 2H), 2.23 (m, 8H), 1.63 (m, 10H), 1.29 (m, 32H). ESMS: 892.3 (M+H$^+$), 914 (M+Na$^+$).

FIG. 1 illustrates this series of reactions. The person of ordinary skill in the art will realize it is possible to manufacture additional ABPs in a manner similar to 1 and utilizing the same principles. Utilizing the same principles as those described above, the following ABPs were also prepared.

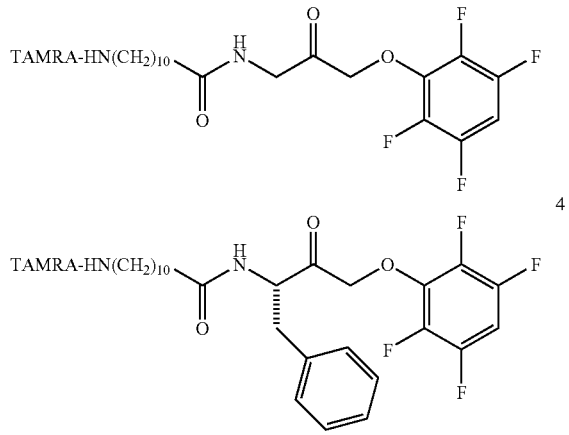

Example 2

Manufacture of Cathepsin-Related Probes 2,6-Bis-trifluoromethyl-benzoicacid-3-(2-amino-3-phenyl-propionylamino)-2-oxo-propyl ester (18)

Composition 17 (150 mg, 0.25 mmol), p-toluenesulfonic acid monohydrate (76 mg, 0.40 mmol, 2 equiv) and MeOH (15 mL) were added to a dry round bottom flask equipped with a magnetic stir bar. The flask was purged several times with $N_2$ and a catalytic amount of 10% Pd on C was added to the reaction. The resulting black heterogeneous mixture was evacuated and charged twice with $H_2$ via a rubber balloon with constant stirring. The reaction was stirred at room temperature for 1.5 h. Upon completion the mixture was filtered through a pad of Celite and concentrated in vacuo to give 18 (94 mg, 0.24 mmol, 99% yield) as a sticky off-white solid. ESMS: 477.8 (M+H$^+$), 499.1 (M+Na$^+$).

2,6-Bis-trifluoromethyl-benzoic acid 3-[2-(11-tert-butoxycarbonylamino-10-methyl-undecanoylamino)-3-phenyl-propionylamino]-2-oxo-propyl ester (19)

Boc-11-amino-undecanoic acid (87 mg, 0.29 mmol, 1.2 equiv), EDAC (69 mg, 0.36 mmol, 1.5 equiv), and HOBt (49 mg, 0.36 mmol, 1.5 equiv) in DMF (10 mL) were added to a dry round bottom flask equipped with a magnetic stir bar. With constant sting was added Composition 18 (94 mg, 0.24 mmol,) and N-methyhnorpholine (twice distilled, 0.9 mL, 0.72 mmol, 3.0 equiv) dissolved in minimal quantity of DMF. The colorless solution slowly turned yellow during the course of the reaction overnight (18 hr). EtOAc (20 mL) was added to the reaction and the organic layer was washed with saturated $NaHCO_3$ (20 mL), $H_2O$ (20 mL), and brine (20 mL), dried over $Na_2SO_4$, and concentrated in vacuo. The resulting oil was purified via column chromatography (silica gel, 1:1, hexanes/EtOAc) to give 19 (63 mg, 0.084 mmol, 24% yield) as a clear, thick oil. ESMS: 746.3 (M+H$^+$), 768.1 (M+Na$^+$).

[9-[4(10-{3-(2,6-Bis-trifluoromethyl-benzoyloxy)-2-oxo-propylcarbamoyl]-2-phenyl-ethylcarbamoyl}-2-carboxy-phenyl]-6-dimethylamino-xanthen-3-yldene}-dimethyl-ammonium (2)

Composition 19 (13 mg, 0.017 mmol) in 4 M HCl/dioxane (2 mL) was added to a dry round bottom flask equipped with a magnetic stir bar. Dry MeOH (0.2 mL) was added to this solution and the reaction was allowed to stir at room temperature for 30 minutes, at which time the solvent was removed in vacuo. The resulting solid was taken up in a minimal amount of DMF and then added dropwise to TAMRA-SE (14 mg, 0.026 mmol, 1.2 equiv.) and DIEA (8 uL, 0.044 mmol, 2.0 equiv) in DMF (~0.2 mL) at room temperature. After 2 hr the reaction solution was diluted with DMSO (1.5 mL) and purified using preparative HPLC at a flow rate of 30 mL/minute and a 90 minute gradient of 0.1% TFA/acetonitrile: 0.1% TFA/water (2-98%) to yield 2 as a bright purple solid. (5 mg, 0.0067 mmol, 31% yield) $^1$H NMR (CD$_3$OD) δ 8.92 (bs, 1H), 8.75 (s, 2H), 8.41 (d, 1H, J=9.2 Hz), 8.26 (d, 1H, J=9 Hz), 8.20 (m, 1H), 8.09 (m, 5H), 7.81 (m, 2H), 8.87 (s, 1H), 7.51 (d, 2H, J=7.6 Hz), 7.14 (d, 4H, J=9.6 Hz), 7.05 (d, 4H, J=9.5 Hz), 6.97 (s, 4H), 5.04 (s, 2H), 4.38 (d, 2H, J=8.1 Hz), 4.18 (d, 2H, J=8.1 Hz), 4.12 (s, 2H), 3.44 (m, 5H), 3.36 (m, 4H), 2.19 (m, 6H), 1.34 (b, 12H), 1.29 (b, 36H). ESMS: 1072.3 (M+H$^+$), 1094.1 (M+Na$^+$)

Figure 2:
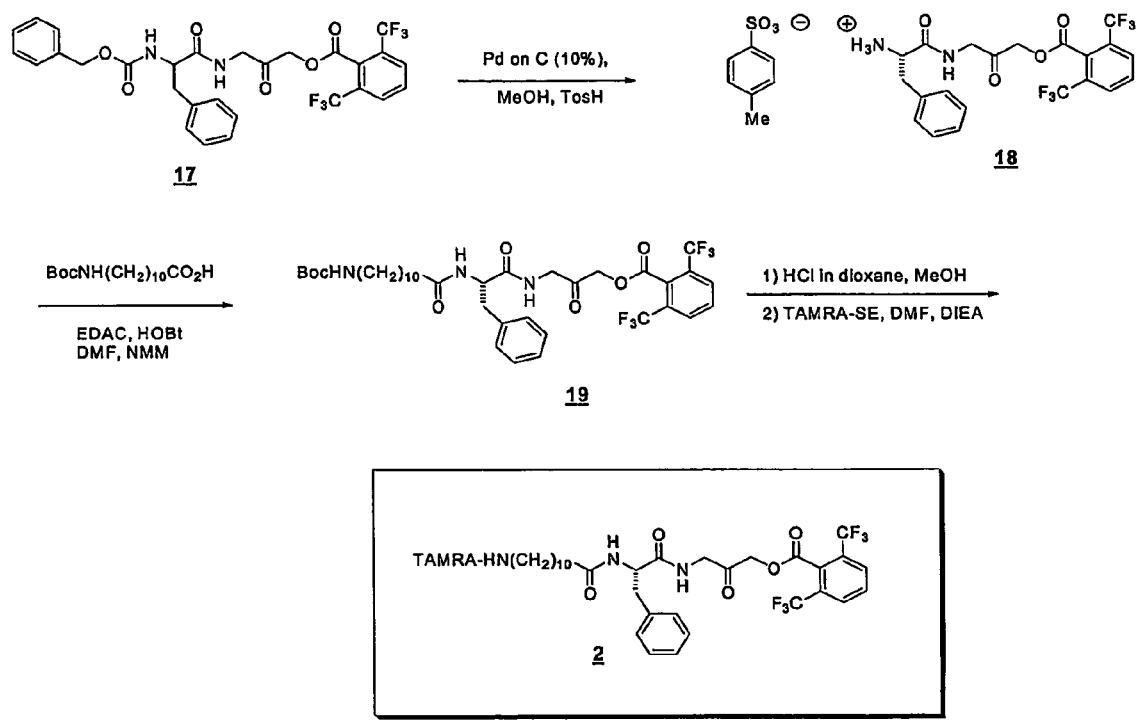
FIG. 2 provides an exemplary synthesis of another exemplary activity based probe of the present invention.

FIG. 2 illustrates this series of reactions. The person of ordinary skill in the art will realize it is possible to manufacture additional ABPs in a manner similar to 2 and utilizing the same principles. Utilizing the same principles as those described above, the following additional ABPs were also prepared:

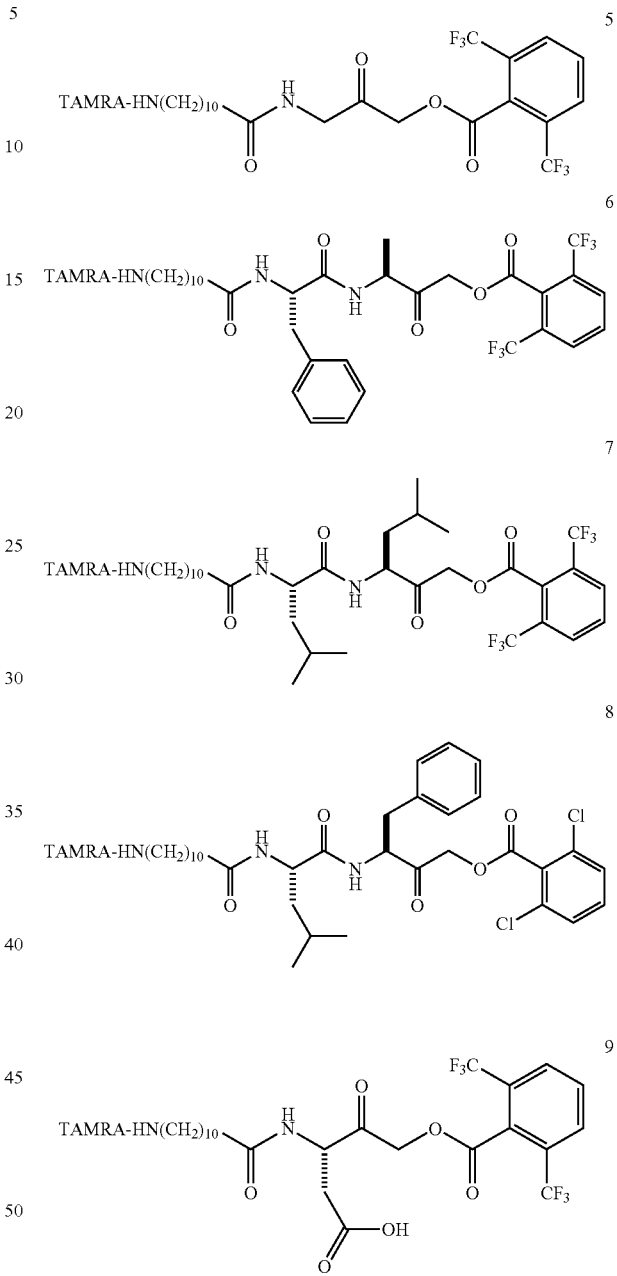

Table 1 provides additional ABPs of the invention.

TABLE 1

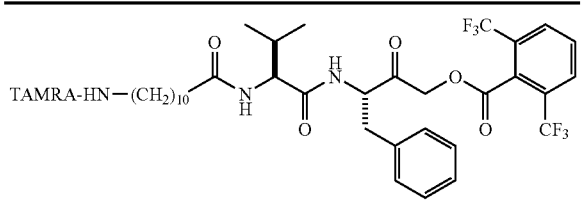

TABLE 1-continued
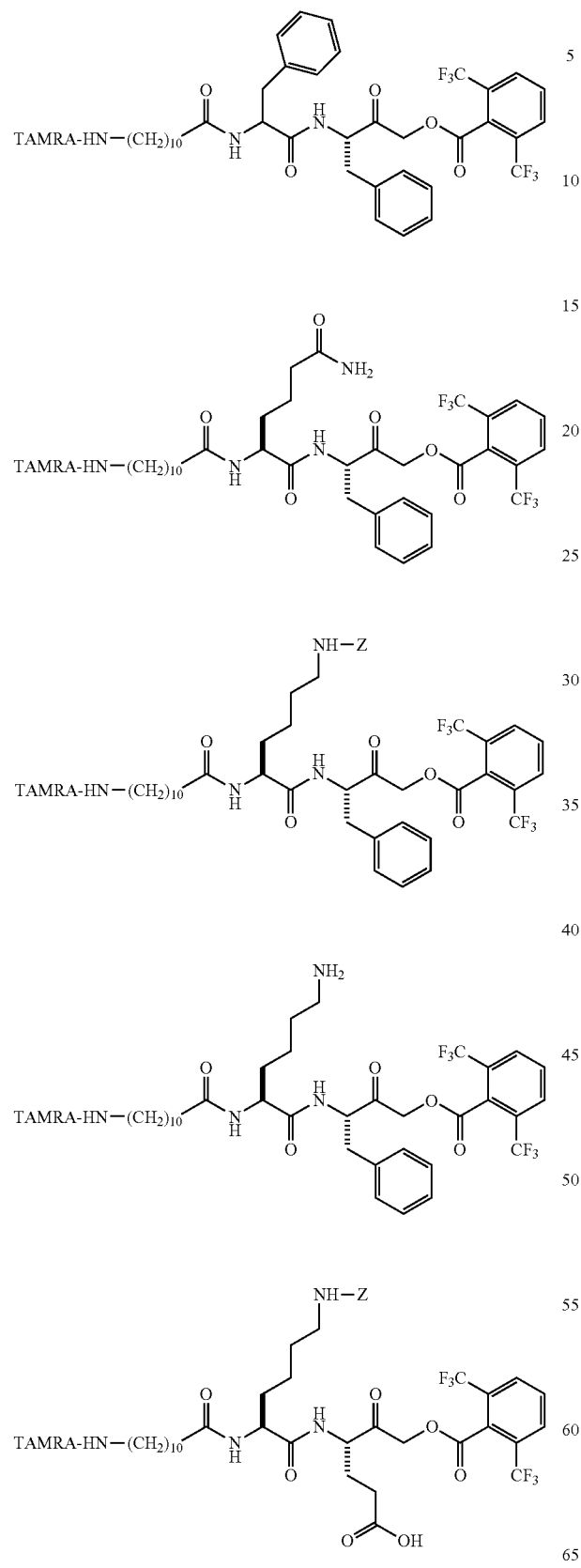
TABLE 1-continued
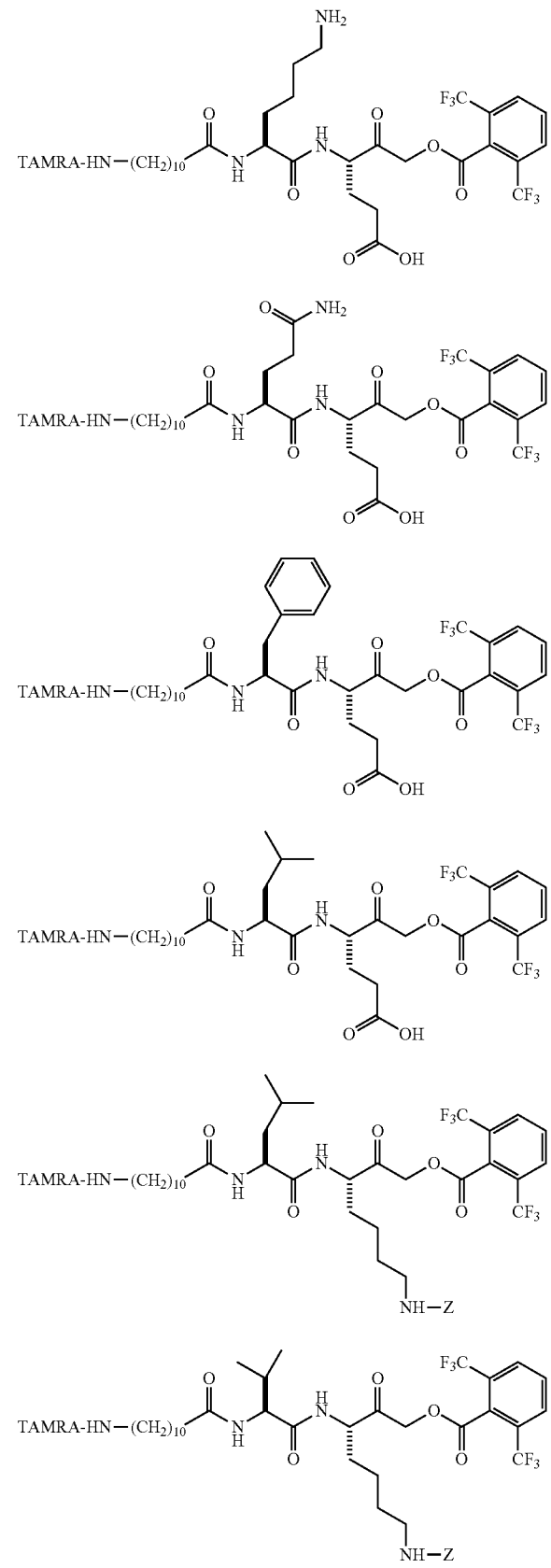

TABLE 1-continued
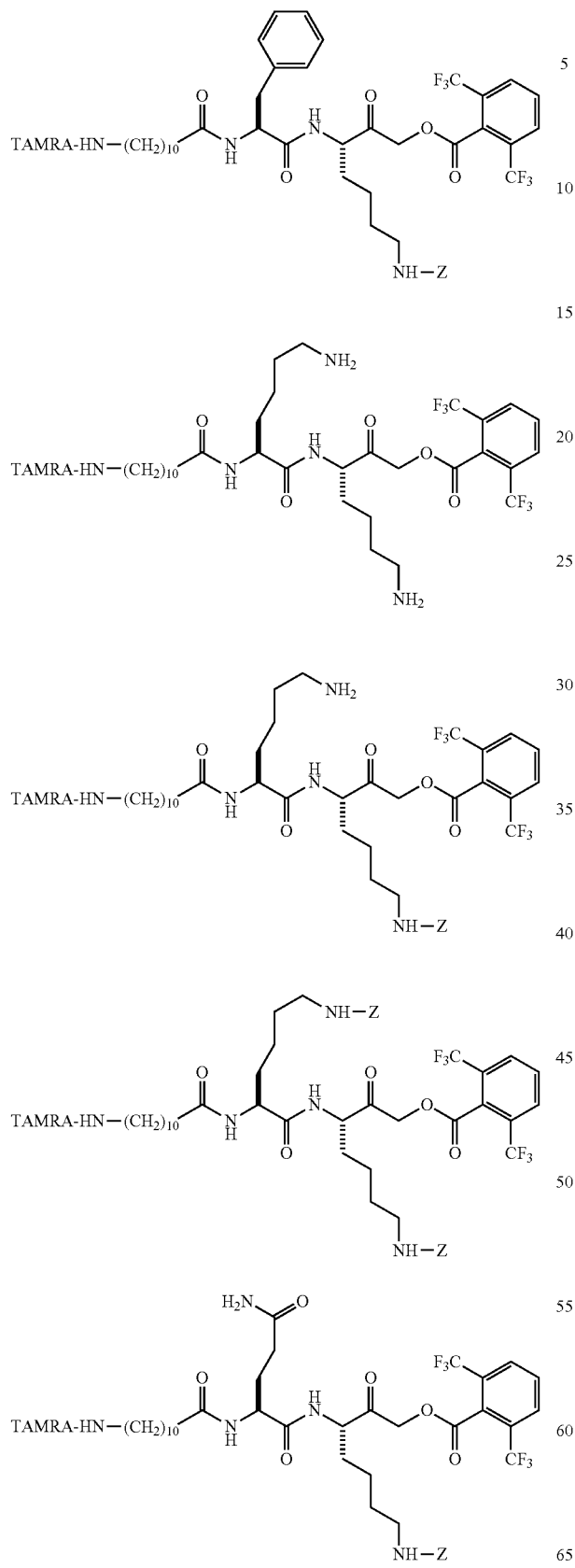
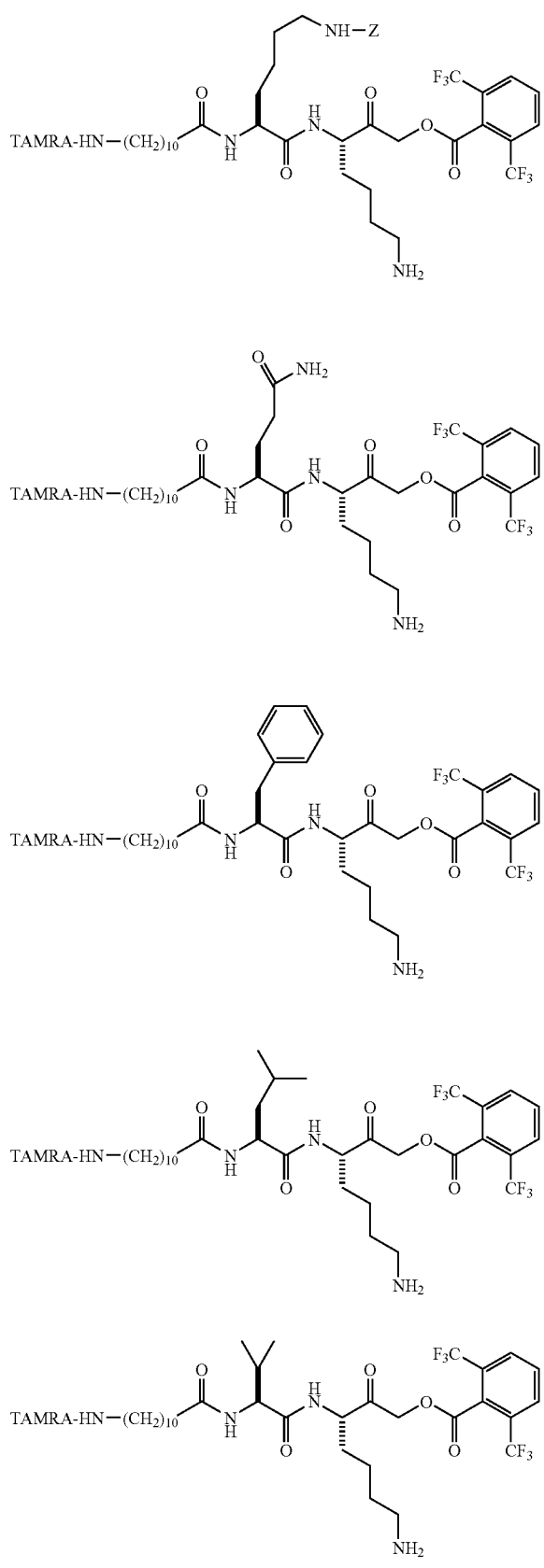

TABLE 1-continued
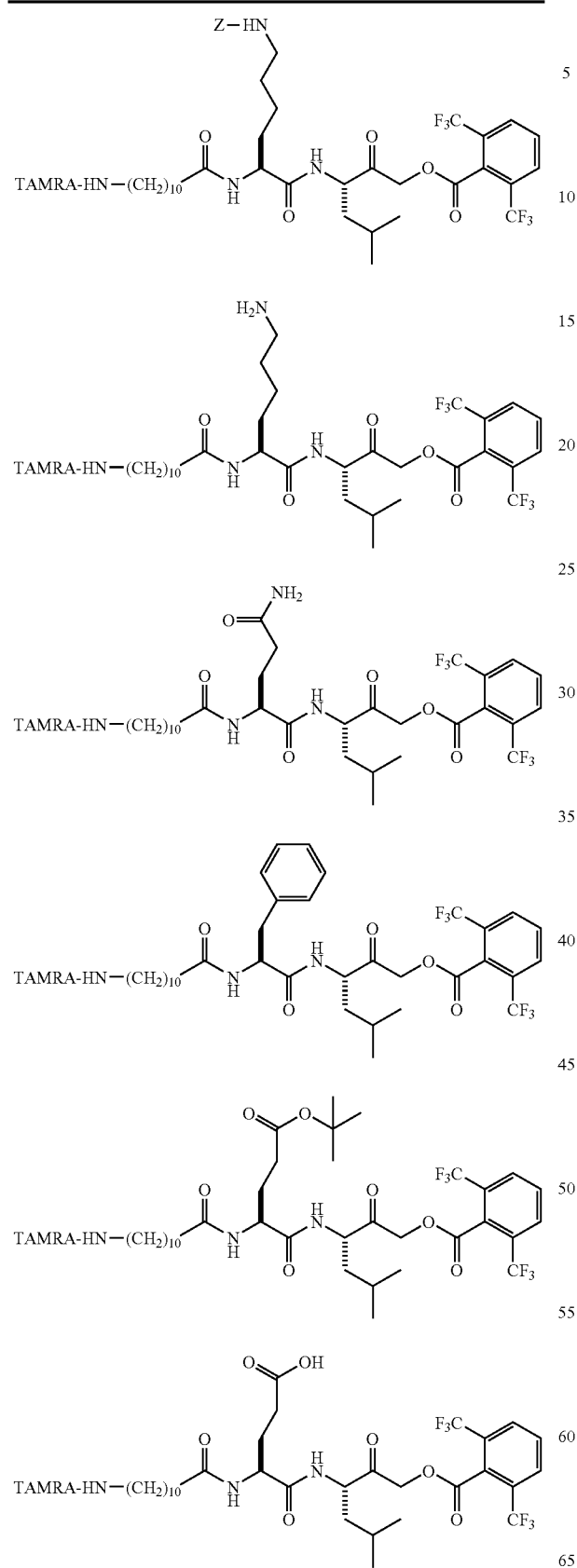
TABLE 1-continued
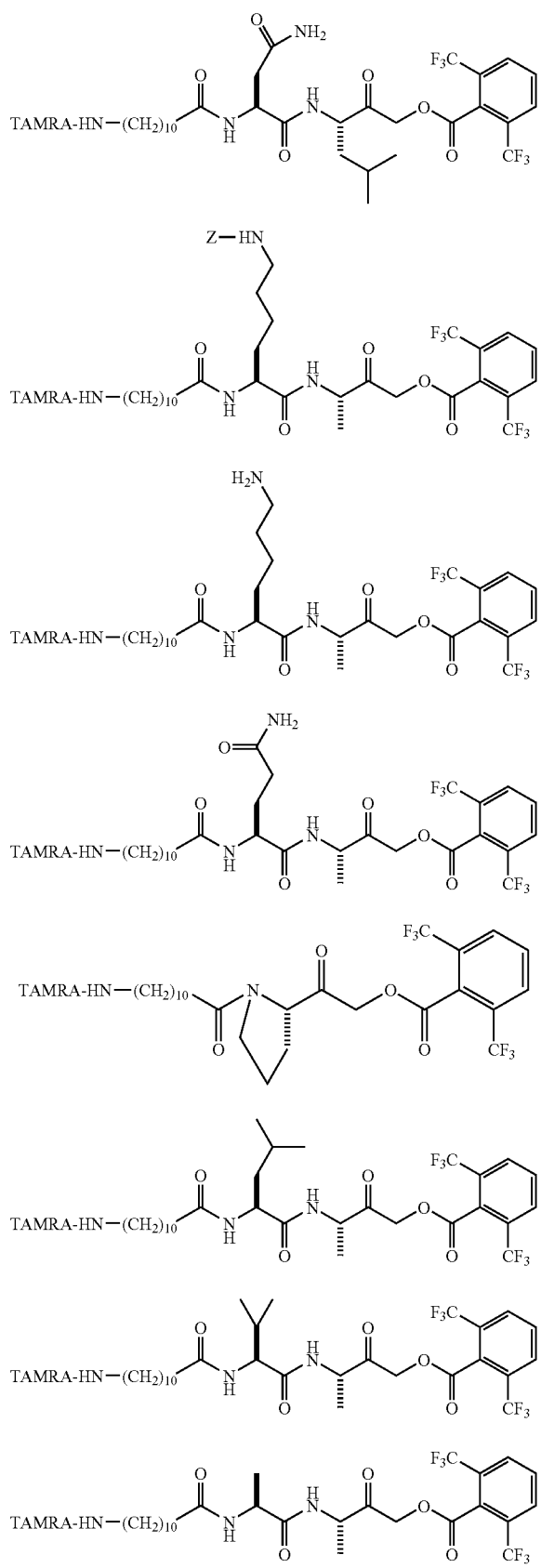

TABLE 1-continued

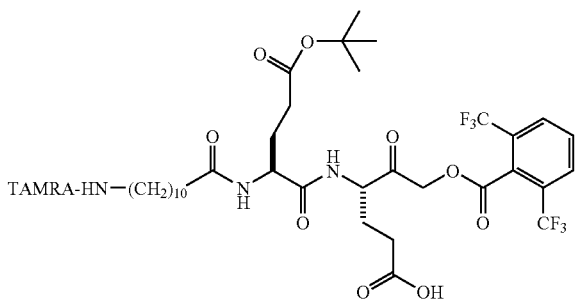
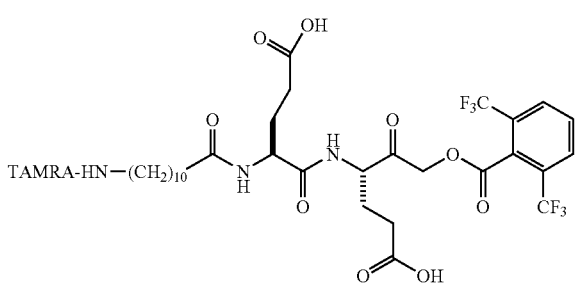
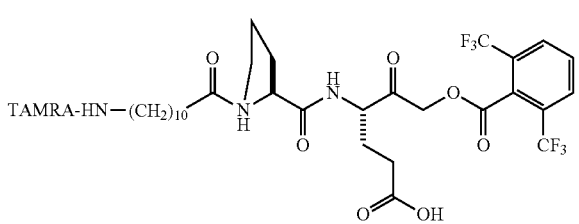
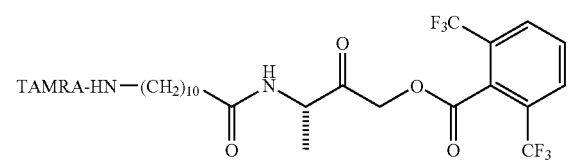
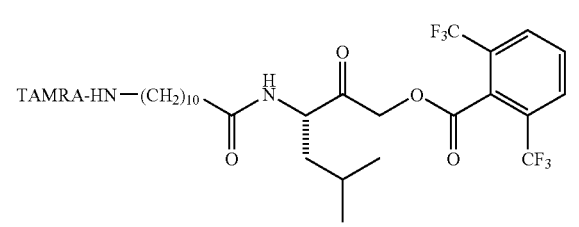
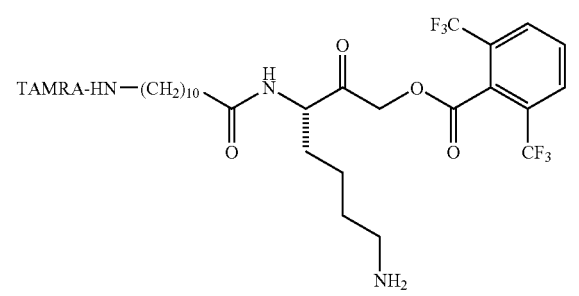

TABLE 1-continued

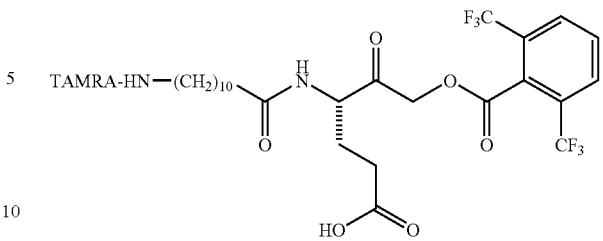

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

The invention claimed is:

1. An activity based probe (ABP) having the structure,

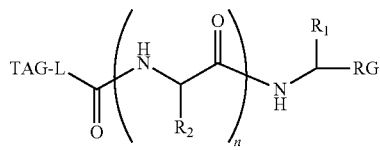

wherein each $R_1$ and $R_2$ is independently selected from the group consisting of:

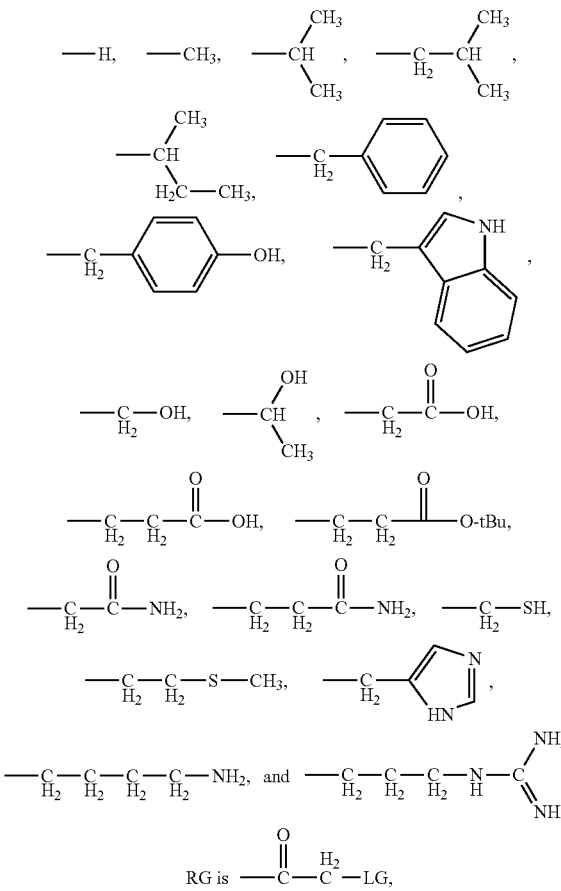

RG is

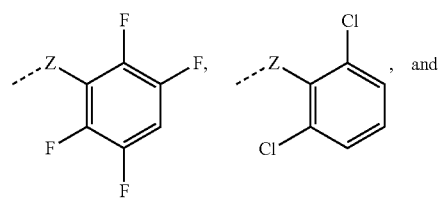

wherein LG is selected from the group consisting of:

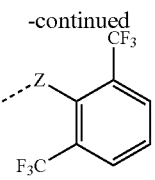

wherein Z is —O— or —O—C(O)—;
L is optionally present and is an alkyl or heteroalkyl group of 1-20 backbone atoms selected from the group consisting of: —N(R)—, —O—, —S— or —C(R)(R)—, where each R is independently H or a —$C_{1-6}$ alkyl straight or branched chain;
TAG is:

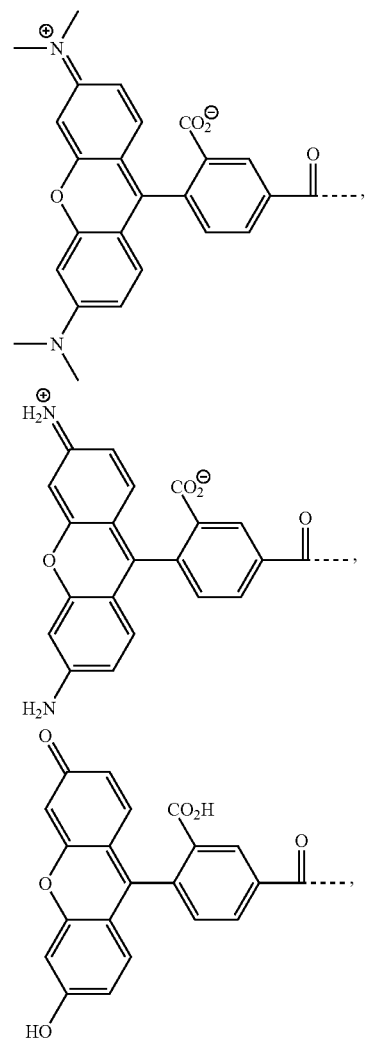

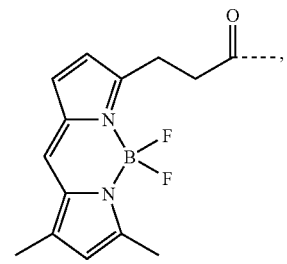

33
-continued
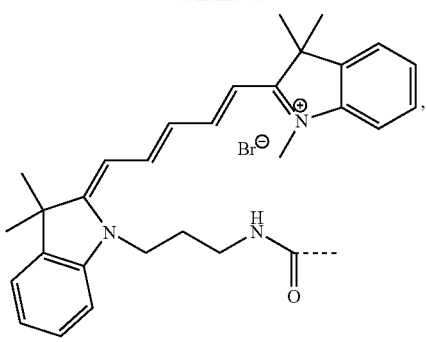
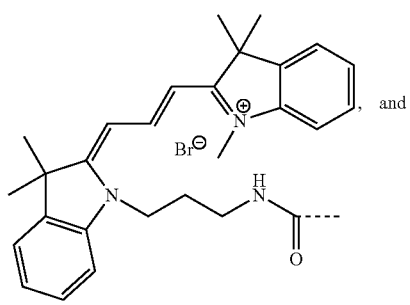
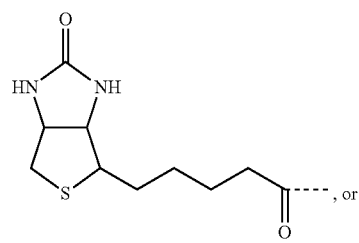, or
desthiobiotin, and
n is an integer from 0 to 4;
or a pharmaceutically acceptable salt or complex thereof.
2. An activity based probe having a structure selected from the group consisting of:
1
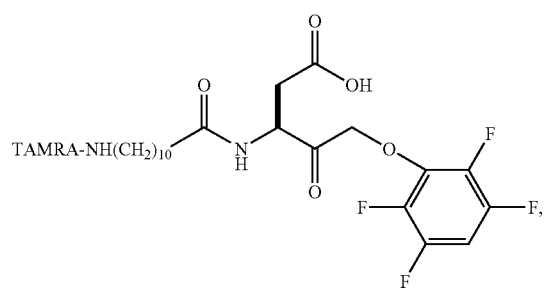
2
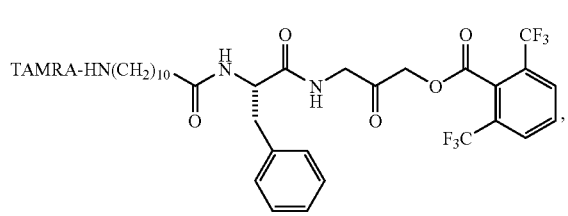
34
-continued
3
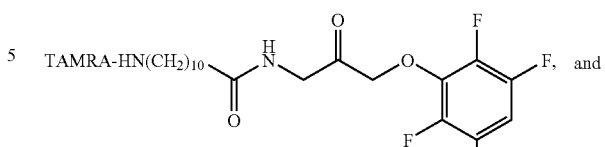, and
4
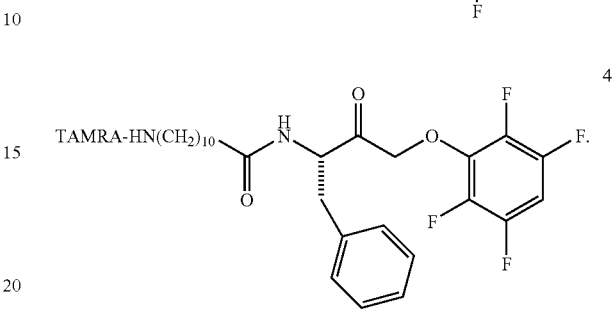
3. An activity based probe having a structure selected from the group consisting of:
5
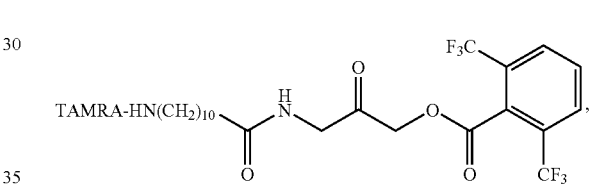
6
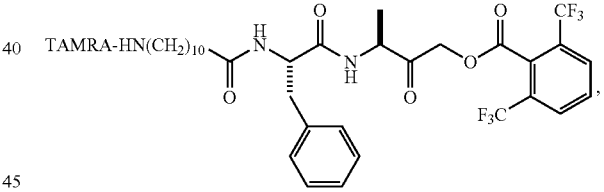
7
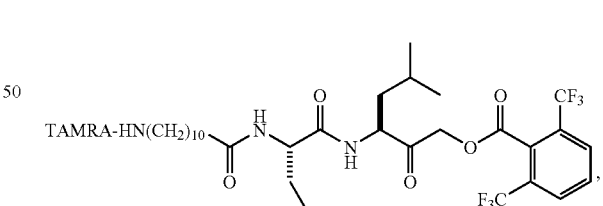
8
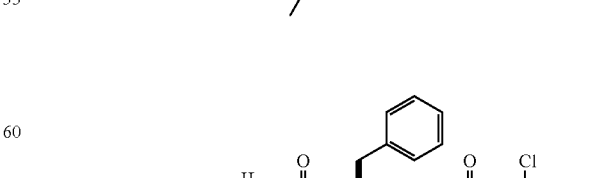, and
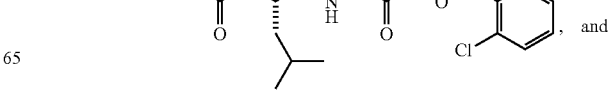

-continued

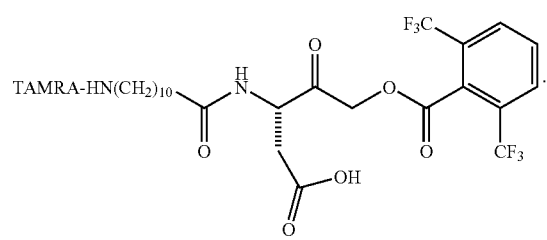

4. An activity based probe library comprising a plurality of activity based probe(s) of claim 1.

5. An activity based probe library comprising a plurality of activity based probe(s) of claim 2.

6. An activity based probe library comprising a plurality of activity based probe(s) of claim 3.

7. An activity based probe having a structure selected from the group consisting of:

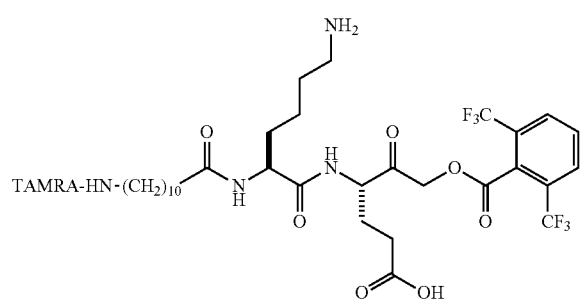

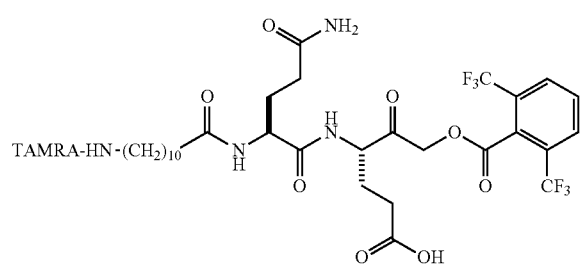

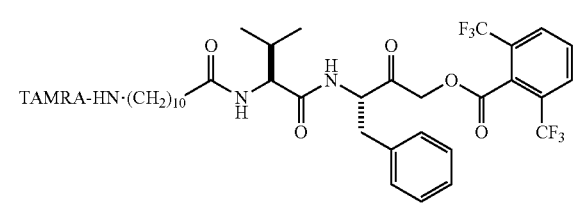

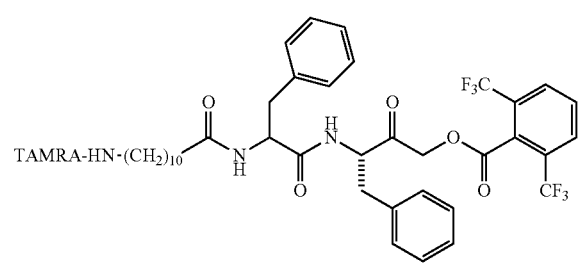

-continued

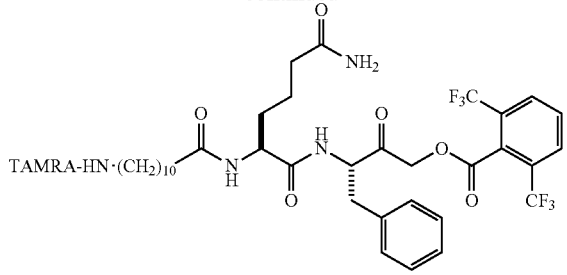

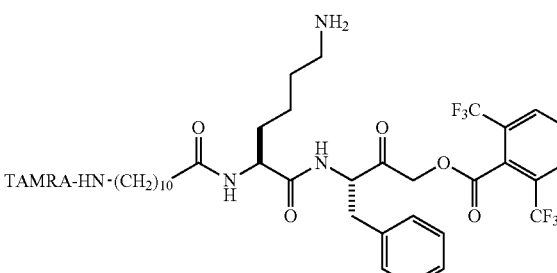

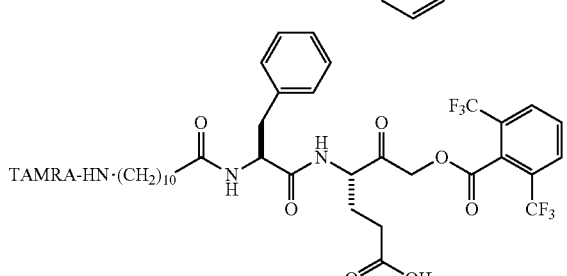

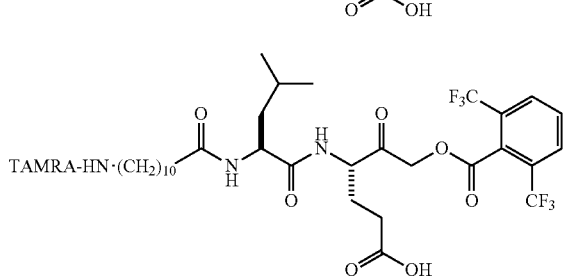

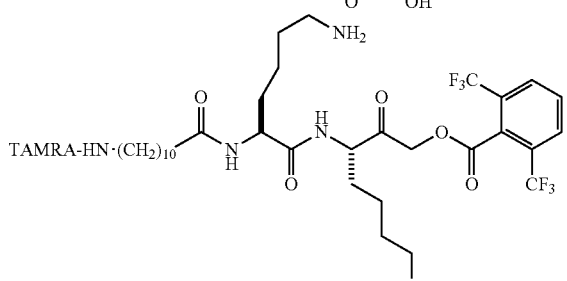

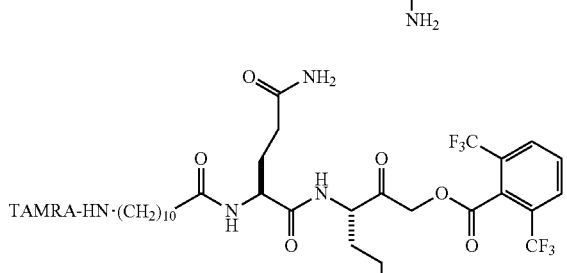

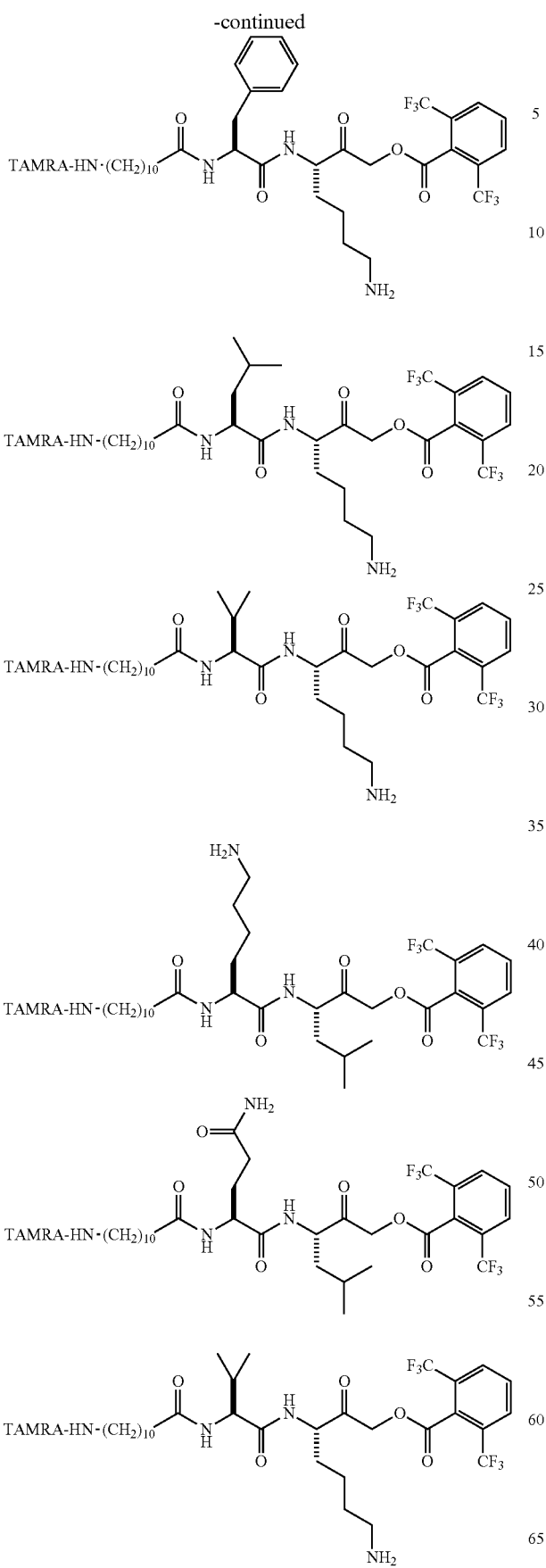
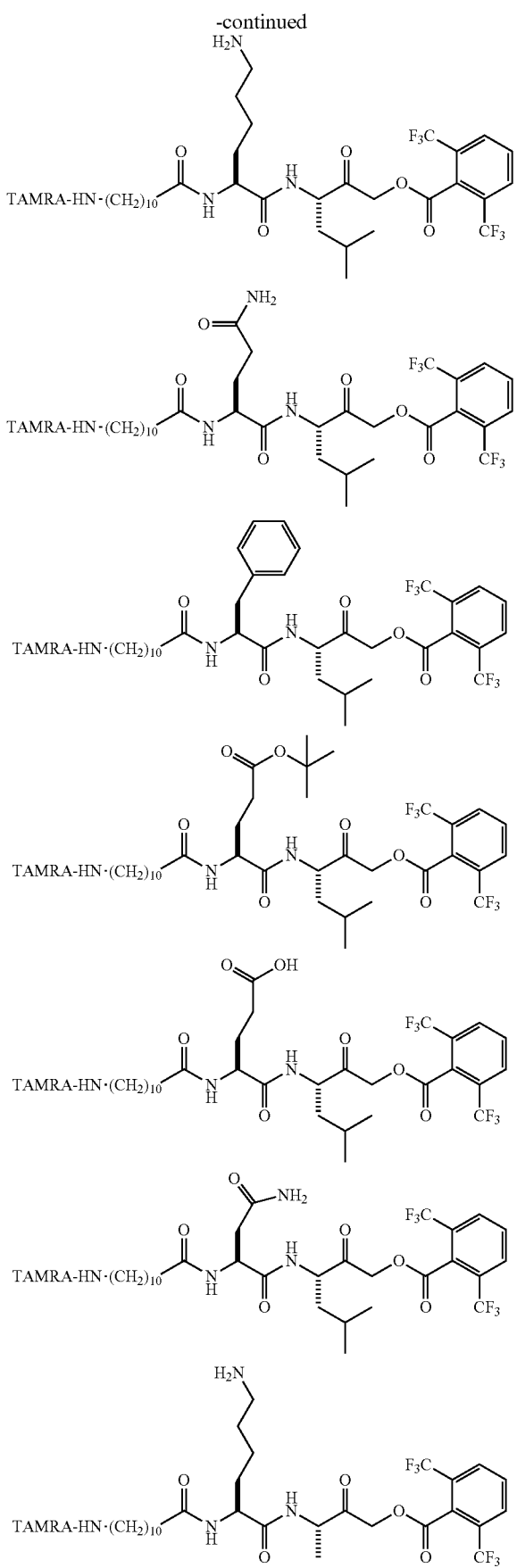

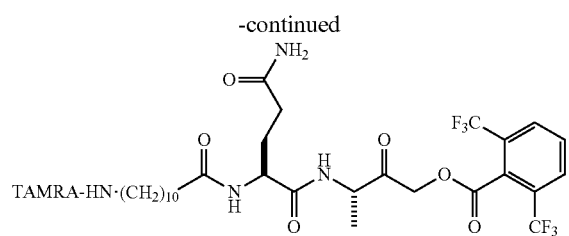
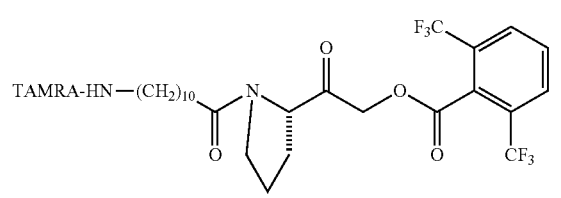
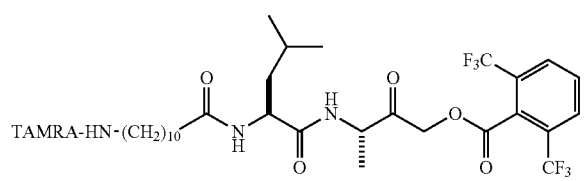
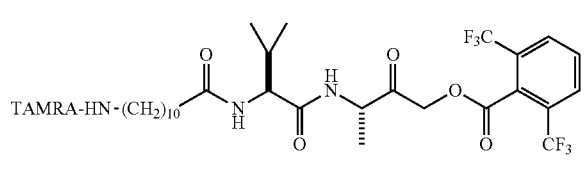
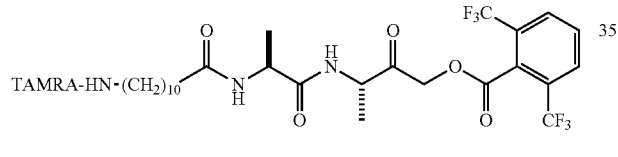
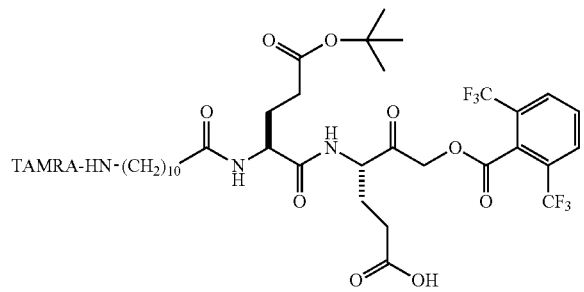
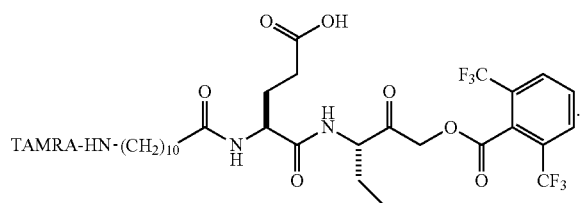
8. An activity based probe according to claim 1 having a structure selected from the group consisting of:
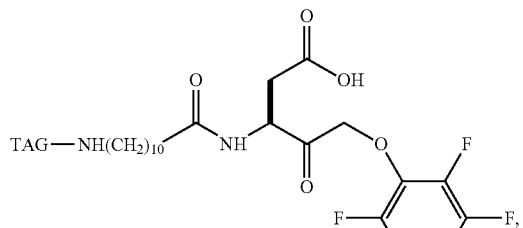
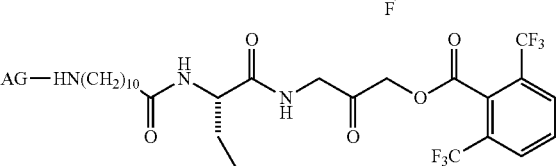
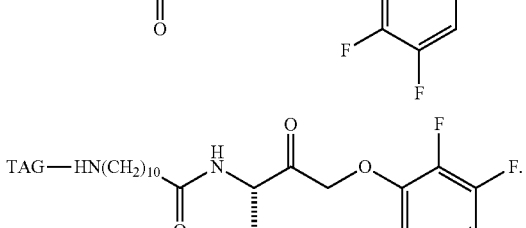
9. An activity based probe according to claim 1 having a structure selected from the group consisting of:
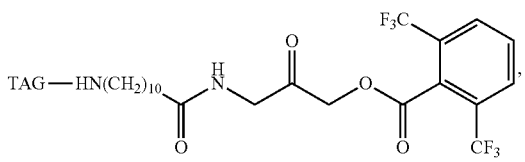
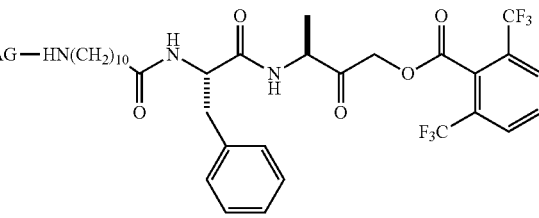
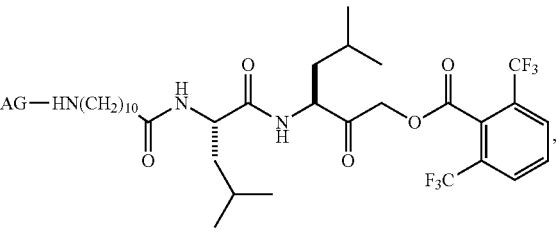

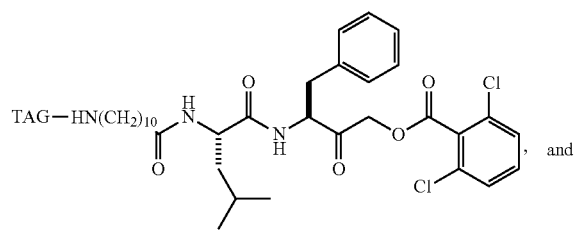
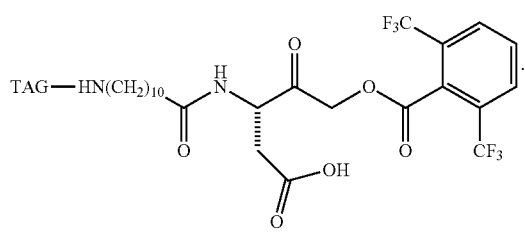
10. An activity based probe according to claim 1 having a structure selected from the group consisting of:
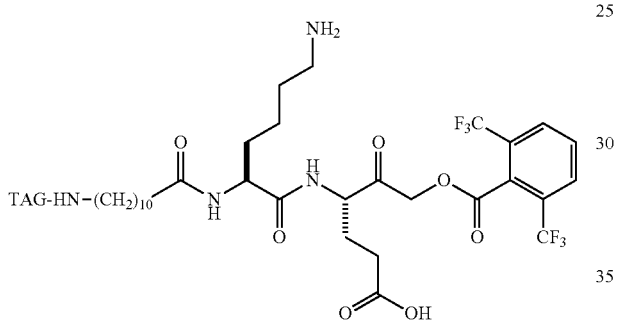
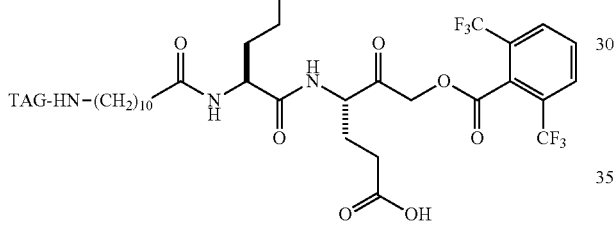
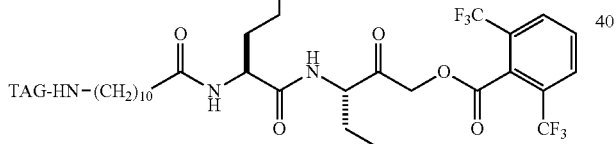
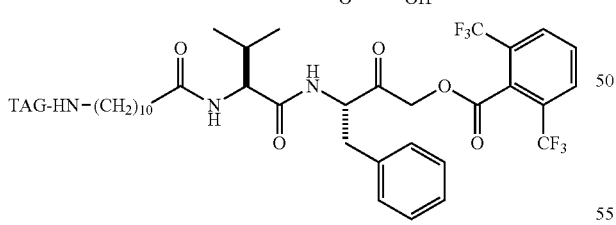
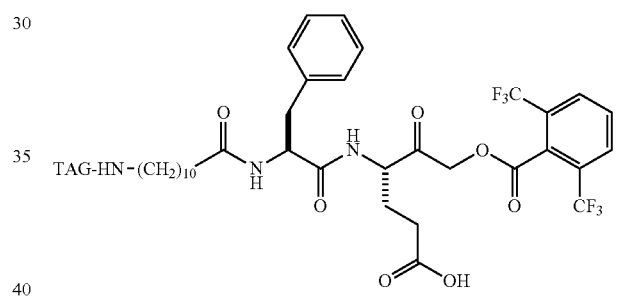
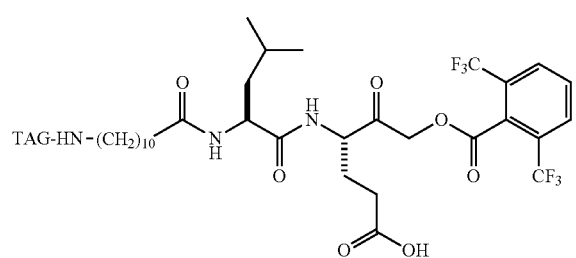
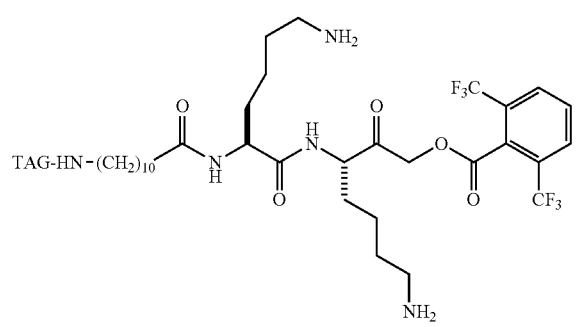

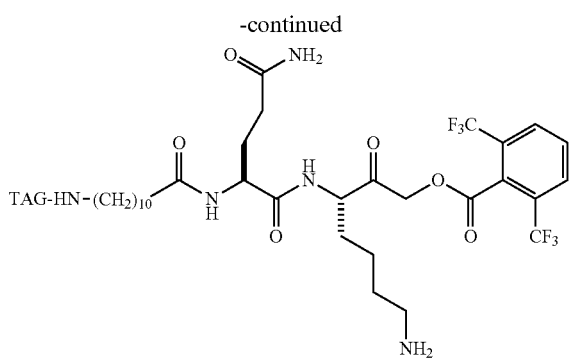
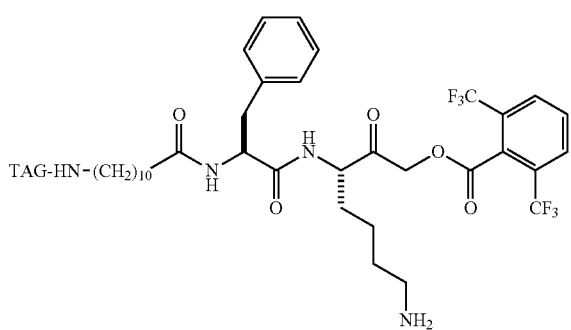
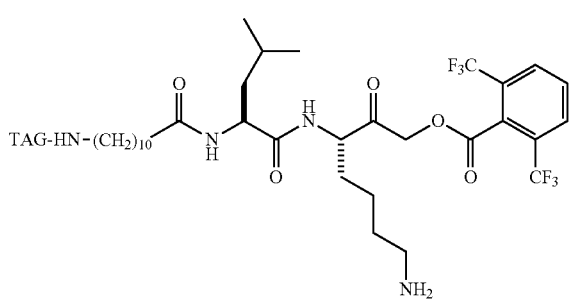
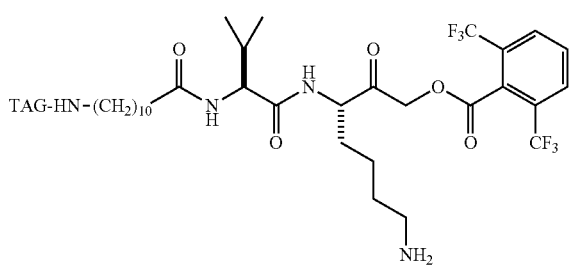
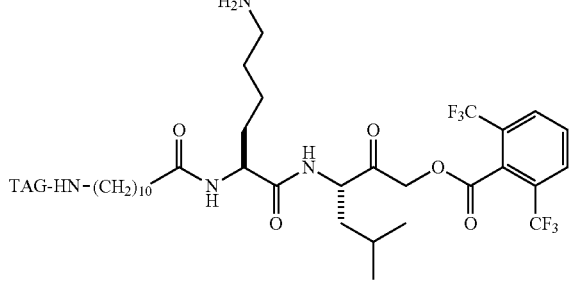
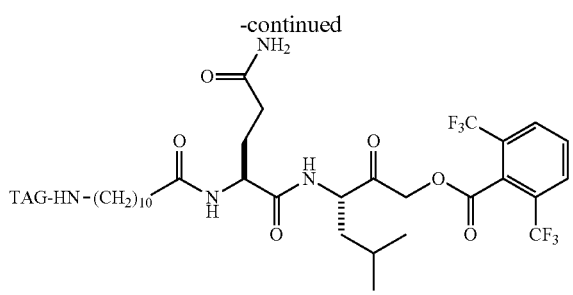
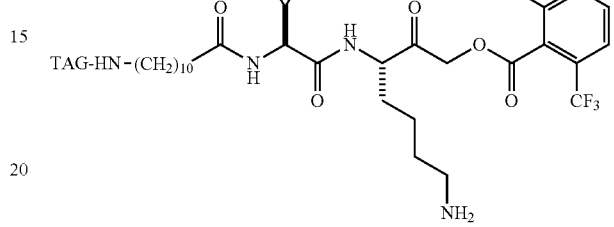
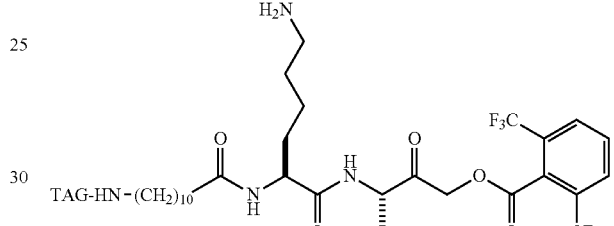
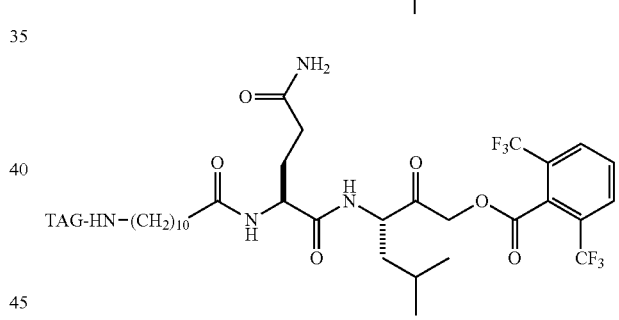
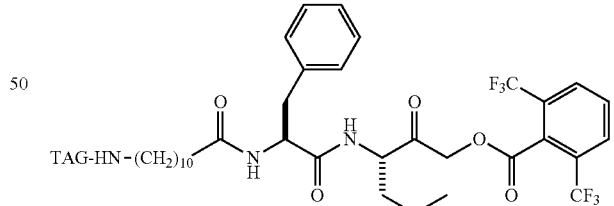
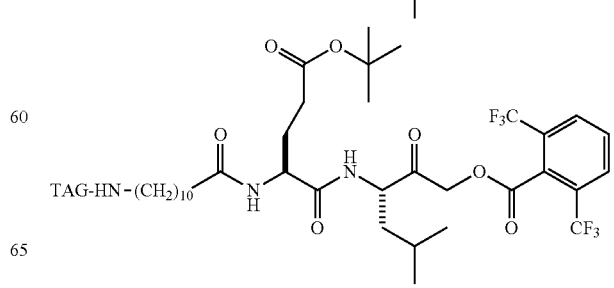

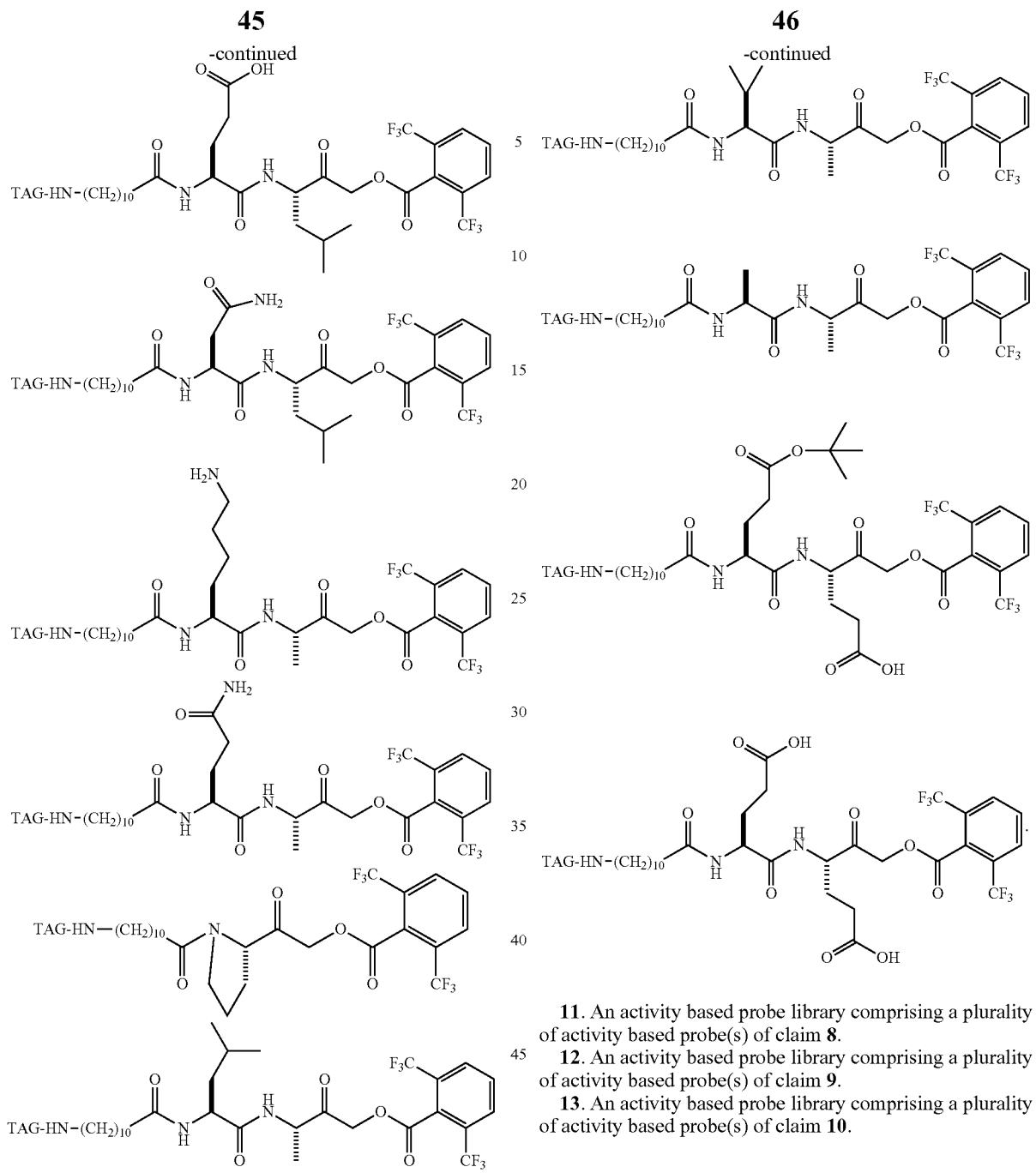
11. An activity based probe library comprising a plurality of activity based probe(s) of claim 8.
12. An activity based probe library comprising a plurality of activity based probe(s) of claim 9.
13. An activity based probe library comprising a plurality of activity based probe(s) of claim 10.
* * * * *